(12) United States Patent
Mou et al.

(10) Patent No.: US 11,772,029 B2
(45) Date of Patent: *Oct. 3, 2023

(54) GAS DETECTION AND PURIFICATION DEVICE

(71) Applicant: MICROJET TECHNOLOGY CO., LTD., Hsinchu (TW)

(72) Inventors: Hao-Jan Mou, Hsinchu (TW);
Ching-Sung Lin, Hsinchu (TW);
Chin-Chuan Wu, Hsinchu (TW);
Yung-Lung Han, Hsinchu (TW);
Chi-Feng Huang, Hsinchu (TW);
Chun-Yi Kuo, Hsinchu (TW);
Chin-Wen Hsieh, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 284 days.

This patent is subject to a terminal disclaimer.

(21) Appl. No.: 17/089,825

(22) Filed: Nov. 5, 2020

(65) Prior Publication Data
US 2021/0188050 A1    Jun. 24, 2021

(30) Foreign Application Priority Data

Dec. 20, 2019  (TW) ................................. 108146886
Mar. 20, 2020  (TW) ................................. 109109502

(51) Int. Cl.
*B01D 46/44* (2006.01)
*B60H 3/06* (2006.01)
(Continued)

(52) U.S. Cl.
CPC ....... *B01D 46/442* (2013.01); *B01D 39/2055* (2013.01); *B01D 46/0028* (2013.01);
(Continued)

(58) Field of Classification Search
CPC .......... B60H 3/0078; B60H 2003/0675; B60H 2003/0691; B60H 3/0658; B60H 3/0608;
(Continued)

(56) References Cited

U.S. PATENT DOCUMENTS

| 2011/0042481 A1* | 2/2011 | Kanamori | A61L 9/14 |
| | | | 239/102.1 |
| 2011/0086118 A1* | 4/2011 | Kim | B01D 53/34 |
| | | | 424/769 |

(Continued)

FOREIGN PATENT DOCUMENTS

| AU | WO-2018112507 A1 * | 6/2018 | ............ B01D 46/42 |
| CN | 102038725 A | 5/2011 | |

(Continued)

OTHER PUBLICATIONS

KR101895978B1_ENG (IP.com machine translation of Hyun) (Year: 2018).*

(Continued)

*Primary Examiner* — Gabriel E Gitman
(74) *Attorney, Agent, or Firm* — McClure, Qualey & Rodack, LLP

(57) ABSTRACT

A gas detection and purification device can be placed in an in-car space and includes a housing, a purification module, a gas-guiding unit, and a gas detection module. The housing has a gas inlet and a gas outlet. A gas channel is between the gas inlet and the gas outlet. The purification module is disposed in the gas channel to filter the gas guided into the gas channel. The gas-guiding unit is disposed in the gas channel and at one side of the purification module. The gas-guiding unit guides the gas into the device from the gas inlet, guides the gas to pass through the purification module for performing filtering and purifying, and discharges the gas out from the gas outlet. The gas detection module is (Continued)

disposed in the gas channel to detect the gas guided into the housing to obtain gas detection data.

21 Claims, 32 Drawing Sheets

(51) Int. Cl.
| | |
|---|---|
| *B01D 46/00* | (2022.01) |
| *B60H 3/00* | (2006.01) |
| *B01D 39/20* | (2006.01) |
| *F24F 8/80* | (2021.01) |
| *F24F 8/10* | (2021.01) |
| *B01D 46/46* | (2006.01) |
| *F24F 110/00* | (2018.01) |

(52) U.S. Cl.
CPC ....... *B01D 46/0032* (2013.01); *B60H 3/0078* (2013.01); *B60H 3/0658* (2013.01); *F24F 8/10* (2021.01); *F24F 8/80* (2021.01); *A61L 2209/111* (2013.01); *B01D 46/46* (2013.01); *B01D 2239/0442* (2013.01); *B01D 2239/0478* (2013.01); *B60H 3/0608* (2013.01); *B60H 2003/0675* (2013.01); *B60H 2003/0691* (2013.01); *F24F 2110/00* (2018.01)

(58) Field of Classification Search
CPC .. F24F 8/10; F24F 8/80; F24F 2110/66; F24F 2110/00; F24F 2110/64; A47L 9/2815; B01D 39/04; B01D 39/2055; B01D 46/0028; B01D 46/0032; B01D 46/0049; B01D 46/442; B01D 46/46; B01D 53/30; B01D 53/323; B01D 2239/0442; B01D 2239/0478; B01D 2259/818; B01D 2257/708; B01D 2255/802; A61L 2209/111; G01N 2015/0693; G01N 15/06
See application file for complete search history.

(56) References Cited

U.S. PATENT DOCUMENTS

| | | | | |
|---|---|---|---|---|
| 2015/0238041 | A1* | 8/2015 | Deasy | ............... A47J 31/20 426/433 |
| 2017/0275472 | A1* | 9/2017 | Yeung | ............... A01N 65/22 |

FOREIGN PATENT DOCUMENTS

| | | | | | |
|---|---|---|---|---|---|
| CN | 107310351 | A | * | 11/2017 | ........... B60H 3/0608 |
| CN | 109420387 | A | | 3/2019 | |
| CN | 209188372 | U | | 8/2019 | |
| DE | 102017001202 | A1 | * | 8/2018 | ........... A62B 18/025 |
| EP | 3473941 | A1 | * | 4/2019 | ............. A61L 9/205 |
| KR | 20150126328 | A | | 11/2015 | |
| KR | 101895978 | B1 | * | 10/2018 | .......... F21V 33/0088 |
| TW | M553219 | U | | 12/2017 | |
| TW | 567364 | B | * | 9/2018 | ............. G01N 21/17 |
| TW | M567364 | U | | 9/2018 | |
| TW | M576250 | U | | 4/2019 | |
| TW | M576492 | U | | 4/2019 | |
| TW | M581748 | U | | 8/2019 | |
| WO | 2018/112507 | A1 | | 6/2018 | |
| WO | WO-2018112507 | A1 | * | 6/2018 | ............. A61L 9/048 |

OTHER PUBLICATIONS

TWM567364U_ENG (IP.com machine translation of Mou) (Year: 2018).*
CN107310351A_ENG (Espacenet machine translation of Huang) (Year: 2017).*
DE102017001202A1_ENG (Espacenet machine translation of Lang) (Year: 2018).*
TWM567364U_ENG (IP.com translation of Mou) (Year: 2018).*

* cited by examiner

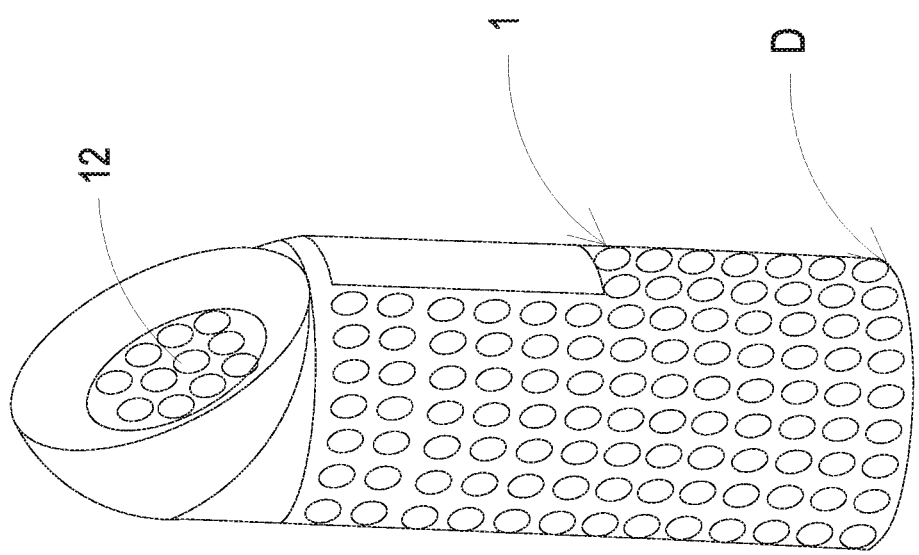

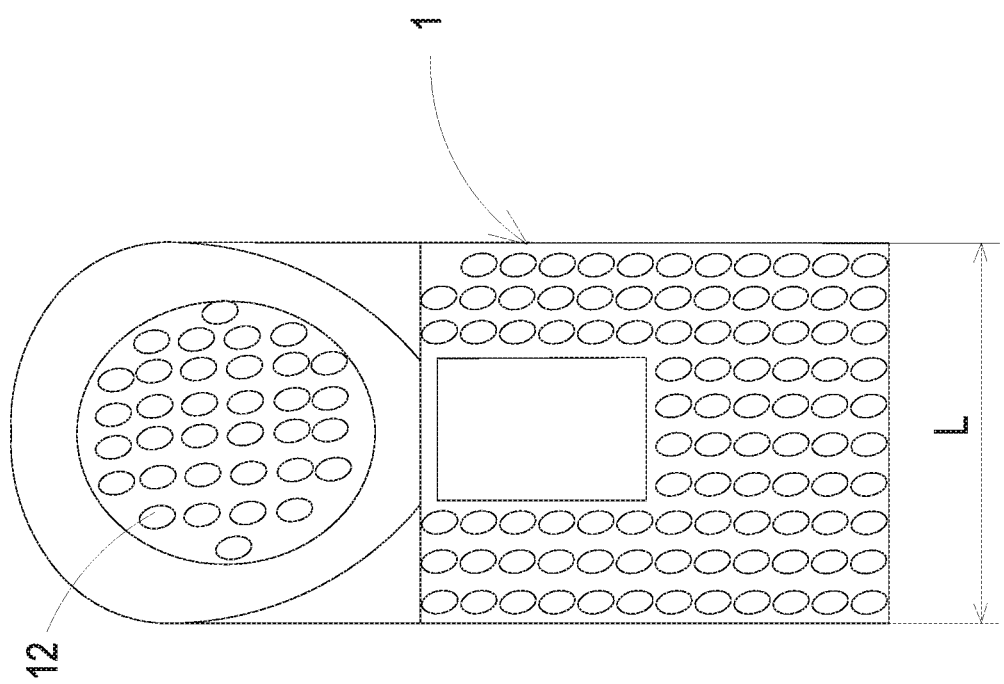

GAS DETECTION AND PURIFICATION DEVICE

CROSS-REFERENCES TO RELATED APPLICATIONS

This non-provisional application claims priority under 35 U.S.C. § 119(a) to Patent Application No. 108146886 filed in Taiwan, R.O.C. on Dec. 20, 2019 and Patent Application No. 109109502 filed in Taiwan, R.O.C. on Mar. 20, 2020, the entire contents of which are hereby incorporated by reference.

BACKGROUND

Technical Field

The present disclosure relates to a gas detection and purification device. In particular, to a gas detection and purification device suitable for being utilized in an in-car space or in an indoor space.

Related Art

At present, people pay more and more attention to monitoring ambient air quality in daily life, such as monitoring carbon monoxide, carbon dioxide, volatile organic compounds (VOC), PM2.5, etc. Moreover, even exposure to these gases can cause adverse health effects on the human body, and can even be life-threatening. Therefore, the quality of ambient air has attracted the attention of various countries. How to implement the monitoring of the quality of ambient air to prevent exposing to hazardous gases becomes a topic that is to be paid attention to.

For the question of how to confirm air quality, it is understood that, it is feasible to use sensors to monitor the ambient gas. Moreover, if the detection information can be provided timely to warn people in a dangerous environment, so they can avoid or escape in time from the health affecting effects and/or injuries caused by the exposure to the ambient gas, then using the sensors to monitor the surrounding environment will be a very good way. The gas detection and purification device is a solution for in-car spaces or for indoor spaces. The gas detection and purification device can detect the air quality anytime and anywhere and can provide purified air, thus being a main topic to be developed.

SUMMARY

One object of the present disclosure is providing a gas detection and purification device. The gas detection and purification device utilizes the gas detection module to detect ambient air quality in the car for the user anytime, and the gas detection and purification device provides a solution for air purification with the purification module.

Accordingly, with the combinational application of the gas detection module and the purification module, the gas detection and purification device prevents the user in the in-car space or in the indoor space from breathing hazardous gases, and the user in the car or the indoor space can obtain information from the device so as to have proper prevention actions according to the notified information.

A general embodiment of the present disclosure provides gas detection and purification device including a housing, a purification module, a gas-guiding unit, and a gas detection module. The housing has at least one gas inlet and at least one gas outlet, and a gas channel is disposed between the at least one gas inlet and the at least one gas outlet. The purification module is disposed in the gas channel so as to filter a gas guided into the gas channel. The gas-guiding unit is disposed in the gas channel and is disposed at one side of the purification module. The gas-guiding unit guides the gas into the gas detection and purification device from the at least one gas inlet, guides the gas to pass through the purification module for performing filtering and purifying, and discharges the gas from the at least one gas outlet into an environment outside the gas detection and purification device. The gas detection module is disposed in the gas channel. The gas detection module includes a control circuit board, a gas detection main body, a microprocessor, a communication device, a power unit, and a battery. The gas detection module is provided for detecting the gas guided into the housing to obtain gas detection data. The gas detection module performs a computation processing to the gas detection data obtained by the gas detection module so as to control the gas-guiding unit to start or to stop operation. When the gas-guiding unit is in operation, the gas-guiding unit guides the gas into the gas detection and purification device from the at least one gas inlet, guides the gas to pass through the purification module for performing filtering and purifying, and discharges the gas from the at least one gas outlet into the environment outside the gas detection and purification device to obtain a purified gas, whereby the gas detection and purification device provides a user with the purified gas.

BRIEF DESCRIPTION OF THE DRAWINGS

The disclosure will become more fully understood from the detailed description given herein below for illustration only, and thus not limitative of the disclosure, wherein:

FIG. 1A illustrates a schematic perspective view of a gas detection and purification device according to an exemplary embodiment of the present disclosure;

FIG. 1B illustrates a schematic perspective view of a gas detection and purification device according to another exemplary embodiment of the present disclosure;

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 2A:
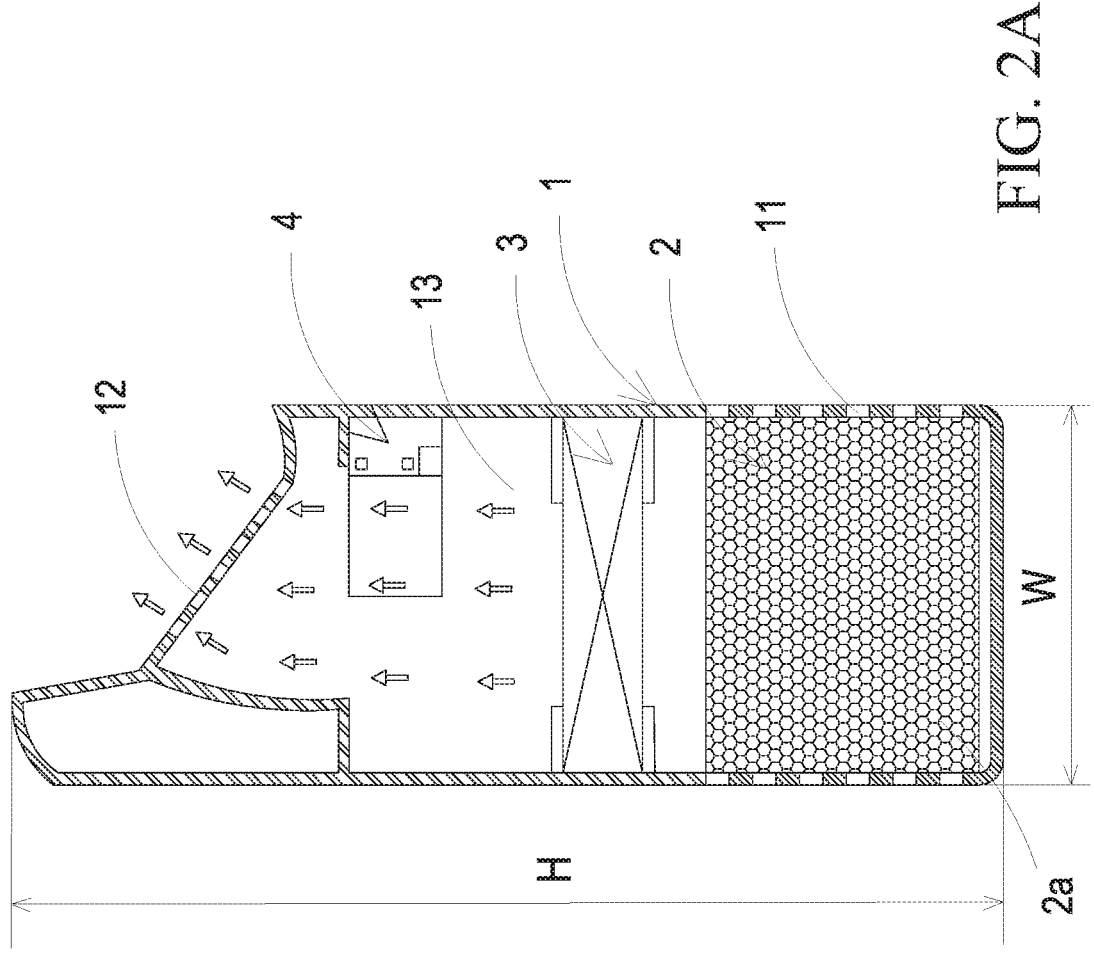
FIG. 2A illustrates a cross-sectional view of the filtering unit of the purification module of the gas detection and purification device according to an exemplary embodiment of the present disclosure.

Please refer to FIG. 1A, FIG. 1B, and FIG. 2A. A gas detection and purification device is provided and includes a housing 1, a purification module 2, a gas-guiding unit 3, and a gas detection module 4. Concerning the portability of the device, the housing 1 has a size suitable for being held and carried. Therefore, the bottom portion of the housing 1 may be of a round cylinder structure (as shown in FIG. 1A) or of a rectangular cylinder structure (as shown in FIG. 1B). Moreover, in the case that the bottom of the housing 1 is of a round cylinder structure, the diameter D of the housing 1 is in a range between 40 mm and 120 mm, and preferably the diameter D of the housing 1 may be 80 mm; the height H of the housing 1 is in a range between 40 mm and 300 mm, and preferably the height of the housing 1 may be 200 mm. While in the case that the bottom of the housing 1 is of a rectangular cylinder structure, the length L of the housing 1 is in a range between 40 mm and 120 mm, and preferably the length L of the housing 1 may be 80 mm; the width W of the housing 1 is in a range between 40 mm and 120 mm, and preferably the width W of the housing 1 may be 80 mm; the height H of the housing 1 is in a range between 100 mm and 300 mm, and preferably the height H of the housing 1 may be 200 mm. Accordingly, the housing 1 is portable and can be placed in an in-car receiving space (not shown). Furthermore, the in-car receiving space may be one of a cup holder, a central console box, a trim platform near a front windshield, and a trim platform near a rear windshield. Alternatively, the housing 1 may be embedded in an in-car space (not shown). Furthermore, the in-car space may be one of a speaker, an air conditioner outlet, a car door trim, an in-car trim, a seat, a headlining, a steering wheel, a receiving box, a rearview mirror, a sun visor, and a central console box. In a further option, the housing 1 may be portable and placed in an in-door space, and the housing 1 of the device is aimed at the user for performing gas detection and purification process for the user.

Moreover, the housing 1 has at least one gas inlet 11 and at least one gas outlet 12. In this embodiment, the housing 1 has a gas inlet 11 and a gas outlet 12, but embodiments are not limited thereto, and a gas channel 13 is disposed between the gas inlet 11 and the gas outlet 12. The purification module 2 is disposed in the gas channel 13 so as to filter a gas guided into the gas channel 13. The gas-guiding unit 3 is disposed in the gas channel 13 and is disposed at one side of the purification module 2. The gas-guiding unit 3 guides the gas into the gas detection and purification device from the gas inlet 11, guides the gas to pass through the purification module 2 for performing filtering and purifying, and discharges the gas from the gas outlet 12 into an environment outside the gas detection and purification device. The gas detection module 4 is disposed in the gas channel 13. The gas detection module 4 is provided for detecting the gas guided into the housing 1 to obtain gas detection data. Accordingly, the gas detection module 4 performs a computation processing to the obtained gas detection data so as to control the gas-guiding unit 3 to start or to stop operation. When the gas-guiding unit 3 is in operation, the gas-guiding unit 3 guides the gas into the gas detection and purification device from the gas inlet 11, guides the gas to pass through the purification module 2 for performing filtering and purifying, and discharges the gas from the gas outlet 12 into the environment outside the gas detection and purification device to obtain a purified gas. Hence, the purified gas is obtained and the gas detection and purification device provides the user with the purified gas. Accordingly, the gas detection and purification device can be placed in the in-car receiving space, in the in-car space, or in the indoor space, and the gas detection and purification device can be provided for detecting ambient air quality in the car or in the indoor space any time, and the gas detection and purification device uses the purification module to provide a solution for air purification in the in-car space or indoor space and prevents the user in the space from breathing hazardous gases.

The purification module 2 is disposed in the gas channel 13, and the purification module 2 may have several embodiments. For example, as shown in FIG. 2A, in this embodiment, the purification module 2 is a filtering unit 2a. The gas is controlled and guided into the gas channel 13 by the gas-guiding unit 3, and the chemical smog, bacteria, dusts, particles, and pollens in the gas are absorbed by the filtering unit 2a, so that the purification module 2 provides a filtering and purifying function for the gas guiding therethrough. The filtering unit 2a may be one of an electrostatic filter, an activated carbon filter, and a high-efficiency particulate air (HEPA) filter. Furthermore, in some embodiments, a purifying factor layer having chlorine dioxide (e.g., AMS) is coated on the filtering unit 2a for suppressing viruses and bacteria in the gas. Accordingly, the suppression rate for influenza A virus, influenza B virus, Enterovirus, and Norovirus exceeds 99%, thereby allowing the reduction of the cross infections of the viruses. In some other embodiments, a herbal protection coating layer consisting of *Rhus chinensis* Mill extracts from Japan and *Ginkgo biloba* extracts may be coated on the filtering unit 2a to form a herbal protection anti-allergy filter. Hence, the herbal protection anti-allergy filter can efficiently perform anti-allergy function and destroy cell surface proteins of influenza viruses (e.g., influenza virus subtype H1N1) passing through the herbal protection anti-allergy filter. In some other embodiments, a layer of silver ions may be coated on the filtering unit 2a for suppressing viruses and bacteria in the gas.

Figure 2B:
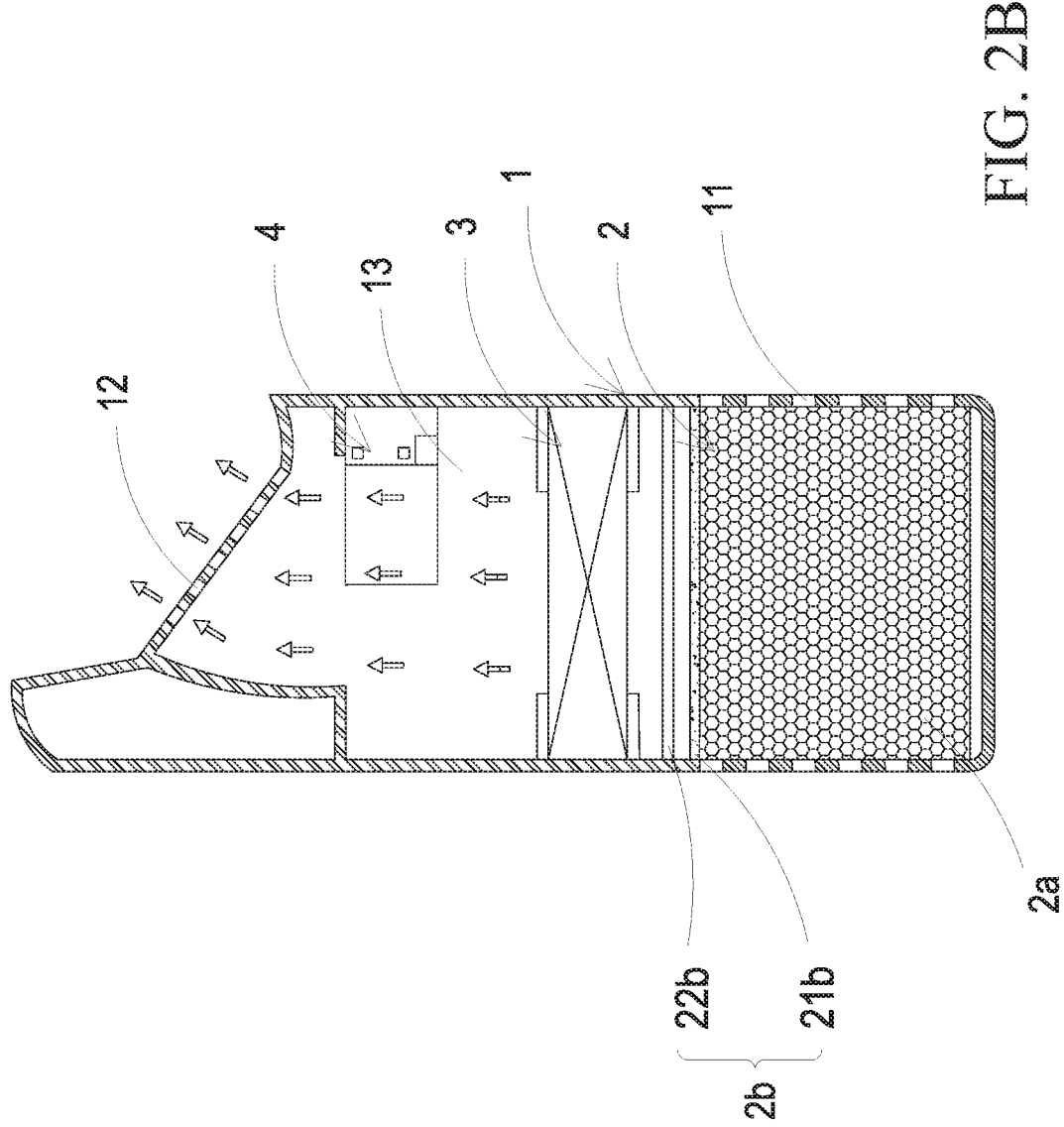
FIG. 2B illustrates a cross-sectional view showing that the purification module includes the filtering unit of FIG. 2A and a photocatalyst unit, according to an exemplary embodiment of the present disclosure.

As shown in FIG. 2B, the purification module 2 may be a combination consisting of the filtering unit 2a and a photocatalyst unit 2b. The photocatalyst unit 2b includes a photocatalyst 21b and an ultraviolet light 22b. The photocatalyst 21b and the ultraviolet light 22b are respectively disposed in the gas channel 13 by a spacing. The gas is guided into the gas channel 13 by the control of the gas-guiding unit 3, and the photocatalyst 21b is excited under illumination of the ultraviolet light 22b to convert the luminous energy into chemical energy, thereby degrading hazardous gases in the gas and sterilizing the gas. Accordingly, the gas guided into the gas detection and purification device is filtered and purified by the purification module 2.

Figure 2C:
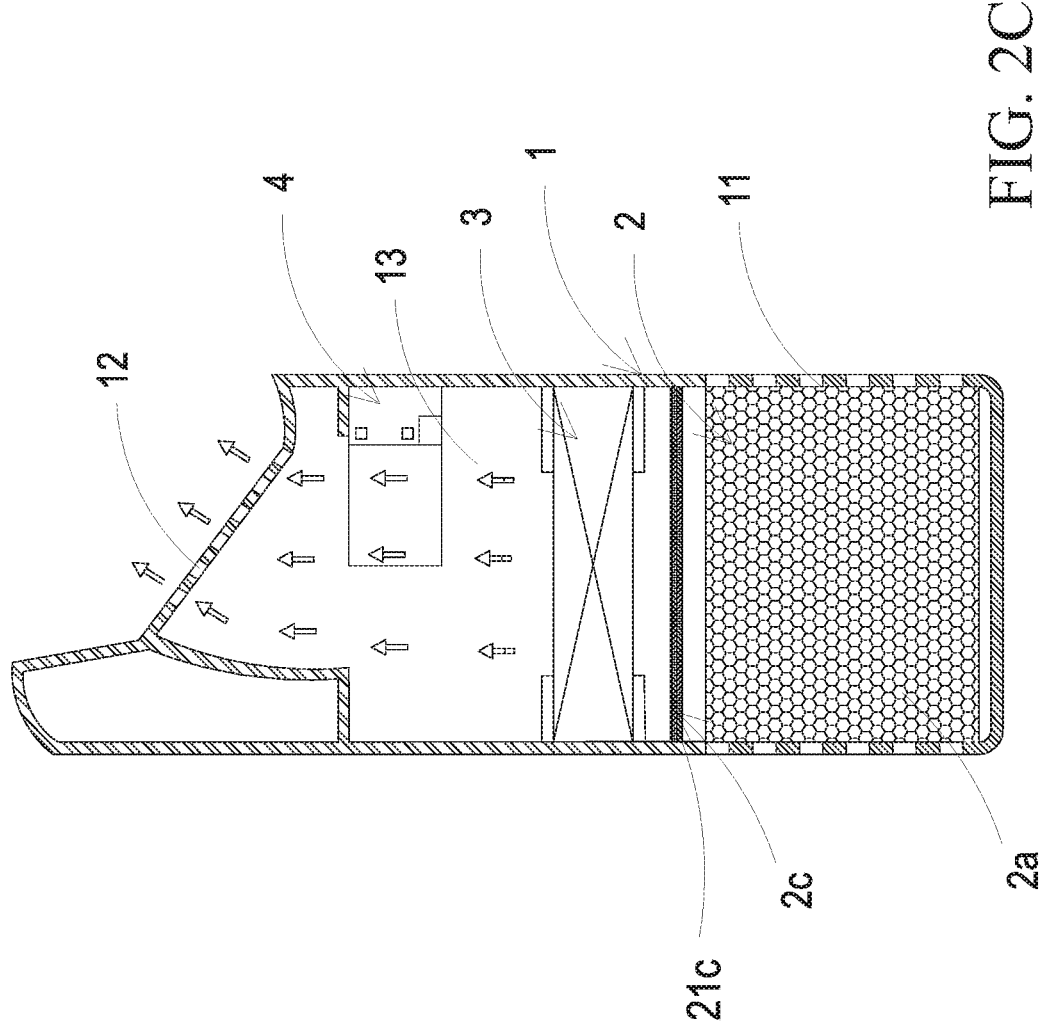
FIG. 2C illustrates a cross-sectional view showing that the purification module includes the filtering unit of FIG. 2A and a photo plasma unit, according to an exemplary embodiment of the present disclosure.

As shown in FIG. 2C, the purification module 2 may be a combination consisting of the filtering unit 2a and a photo plasma unit 2c. The photo plasma unit 2c includes a nanometer optical tube 21c, and the nanometer optical tube 21c is disposed in the gas channel 13. The gas is guided into the gas channel 13 by the control of the gas-guiding unit 3, and the gas is illuminated by the light of the nanometer optical tube 21c, so that the oxygen molecules and water molecules are degraded to form high oxidative photo plasma, thereby forming an plasma stream capable of destroying organic molecules. Accordingly, volatile organic compounds such as formaldehyde and toluene in the gas can be degraded into water and carbon dioxide. Thus, the gas guided into the gas detection and purification device can be filtered and purified by the purification module 2.

Figure 2D:
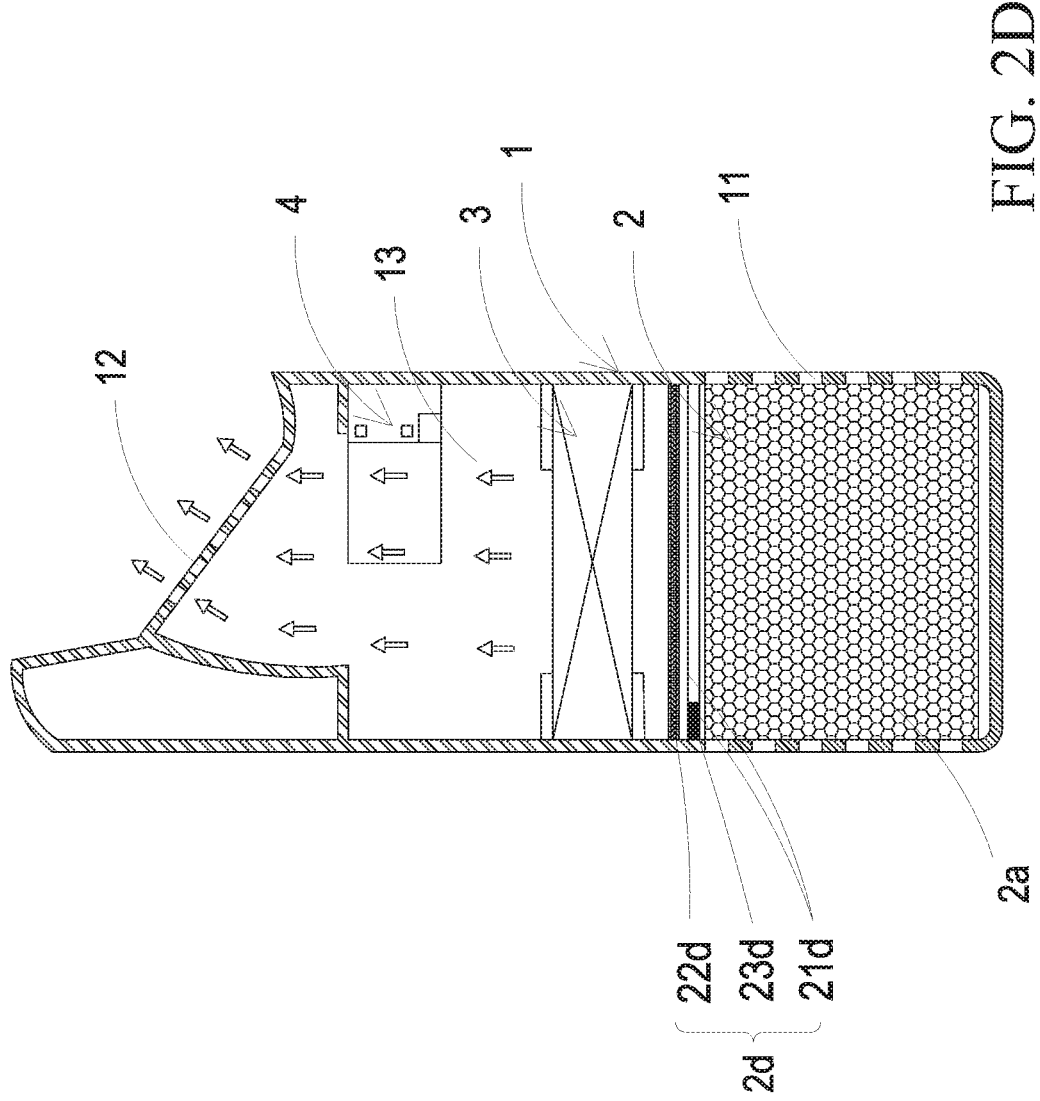
FIG. 2D illustrates a cross-sectional view showing that the purification module includes the filtering unit of FIG. 2A and a negative ion unit, according to an exemplary embodiment of the present disclosure.

As shown in FIG. 2D, the purification module 2 may be a combination consisting of the filtering unit 2a and a negative ion unit 2d. The negative ion unit 2d includes at least one electrode wire 21d, at least one dust-collecting plate 22d, and a boost power supply 23d. The electrode wire 21d and the dust-collecting plate 22d are disposed in the gas channel 13. The boost power supply 23d provides the electrode wire 21d with high voltage electricity. The dust-collecting plate 22d has negative ions thereon. Therefore, upon the gas is guided into the gas channel 13 by the control of the gas-guiding unit 3, the electrode wire 21d discharges electricity under a high voltage, so that particulates having positive ions in the gas are adhered on the dust-collecting plate 22d having negative ions. Accordingly, the gas guided into the gas detection and purification device is filtered and purified by the purification module 2.

Figure 2E:
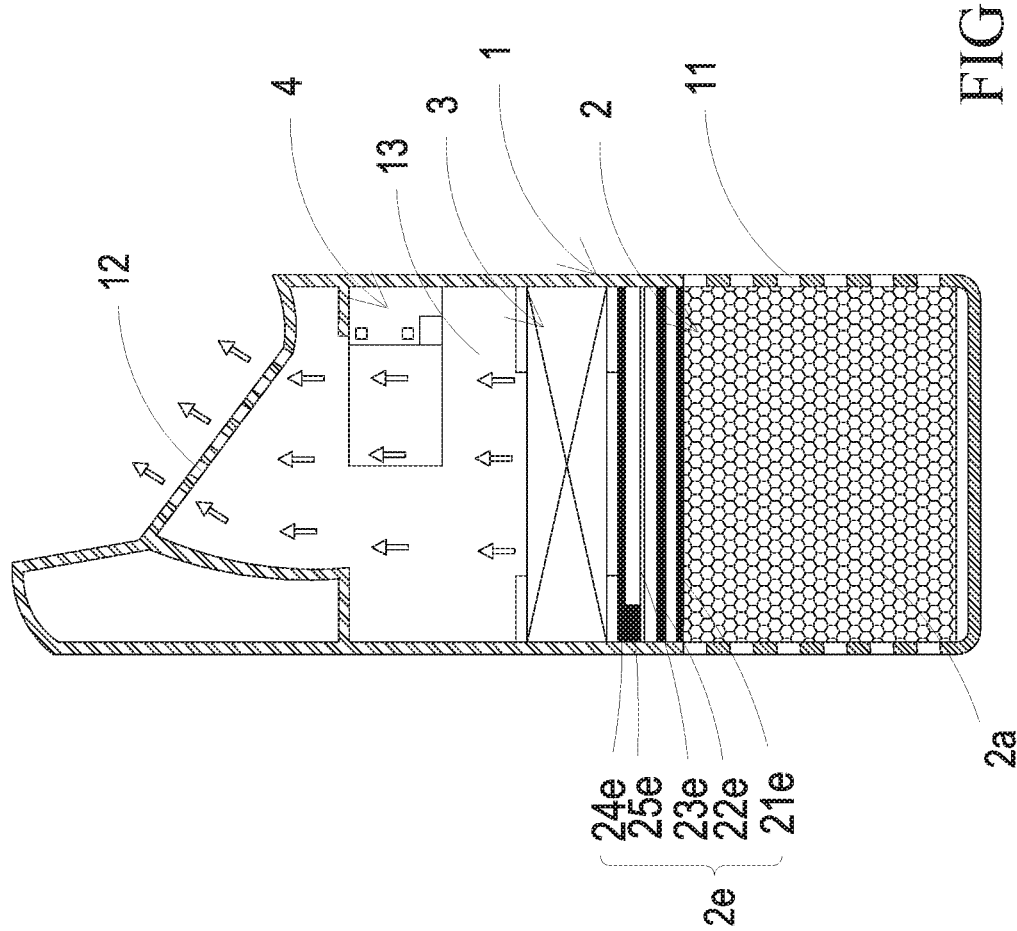
FIG. 2E illustrates a cross-sectional view showing that the purification module includes the filtering unit of FIG. 2A and a plasma unit, according to an exemplary embodiment of the present disclosure, according to an exemplary embodiment of the present disclosure.

As shown in FIG. 2E, the purification module 2 may be a combination consisting of the filtering unit 2a and a plasma unit 2e. The plasma unit 2e includes an electric-field first protection mesh 21e, an absorbing mesh 22e, a high-voltage discharge electrode 23e, an electric-field second protection mesh 24e, and a boost power supply 25e. The electric-field first protection mesh 21e, the absorbing mesh 22e, and the electric-field second protection mesh 23e are disposed in the gas channel 13, and the absorbing mesh 22e and the high-voltage discharge electrode 23e are located between the electric-field first protection mesh 21e and the electric-field second protection mesh 24e. The boost power supply 25e provides the high-voltage discharge electrode 23e with a high voltage so as to generate a high-voltage plasma column. Therefore, upon the gas is guided into the gas channel 13 by the control of the gas-guiding unit 3, the oxygen molecules and the water molecules in the gas are ionized to form cations ($H^+$) and anions ($O_2^-$). After substances which are among the ions and attached by water molecules are attached on the surfaces of viruses and the surfaces of bacteria, the water molecules are converted into oxidative oxygen ions (hydroxyl ions, $OH^-$ ions), and the oxidative oxygen ions take away the hydrogen ions of the proteins on the surfaces of the viruses and the bacteria to degrade the viruses and the bacteria. Accordingly, the gas guided into the gas detection and purification device is filtered and purified by the purification module 2.

The aforementioned gas-guiding unit 3 may be a fan, for example, may be a vortex fan, a centrifugal fan, or the like. Alternatively, as shown in FIG. 3A, FIG. 3B, FIG. 4A, and FIG. 4B, the gas-guiding unit 3 may be an actuation pump 30. The actuation pump 30 is sequentially stacked by an inlet plate 301, a resonance sheet 302, a piezoelectric actuator 303, a first insulation sheet 304, a conductive sheet 305, and a second insulation sheet 306. The inlet plate 301 has at least one inlet hole 301a, at least one convergence channel 301b, and a convergence chamber 301c. The inlet hole 301a is used to guide the gas outside the actuation pump 30 to flow therein. The inlet hole 301a correspondingly penetrates the convergence channel 301b, and the convergence channel 301b is converged at the convergence chamber 301c, so that the gas guided from the inlet hole 301a can be converged at the convergence chamber 301c. In this embodiment, the number of the inlet holes 301a and the number of the convergence channels 301b are the same. Moreover, in this embodiment, the number of the inlet holes 301a and the number of the convergence channels 301b are respectively four, but not limited thereto. The four inlet holes 301a respectively penetrate the four convergence channels 301b, and the four convergence channels 301b are converged at the convergence chamber 301c.

Figure 3A:
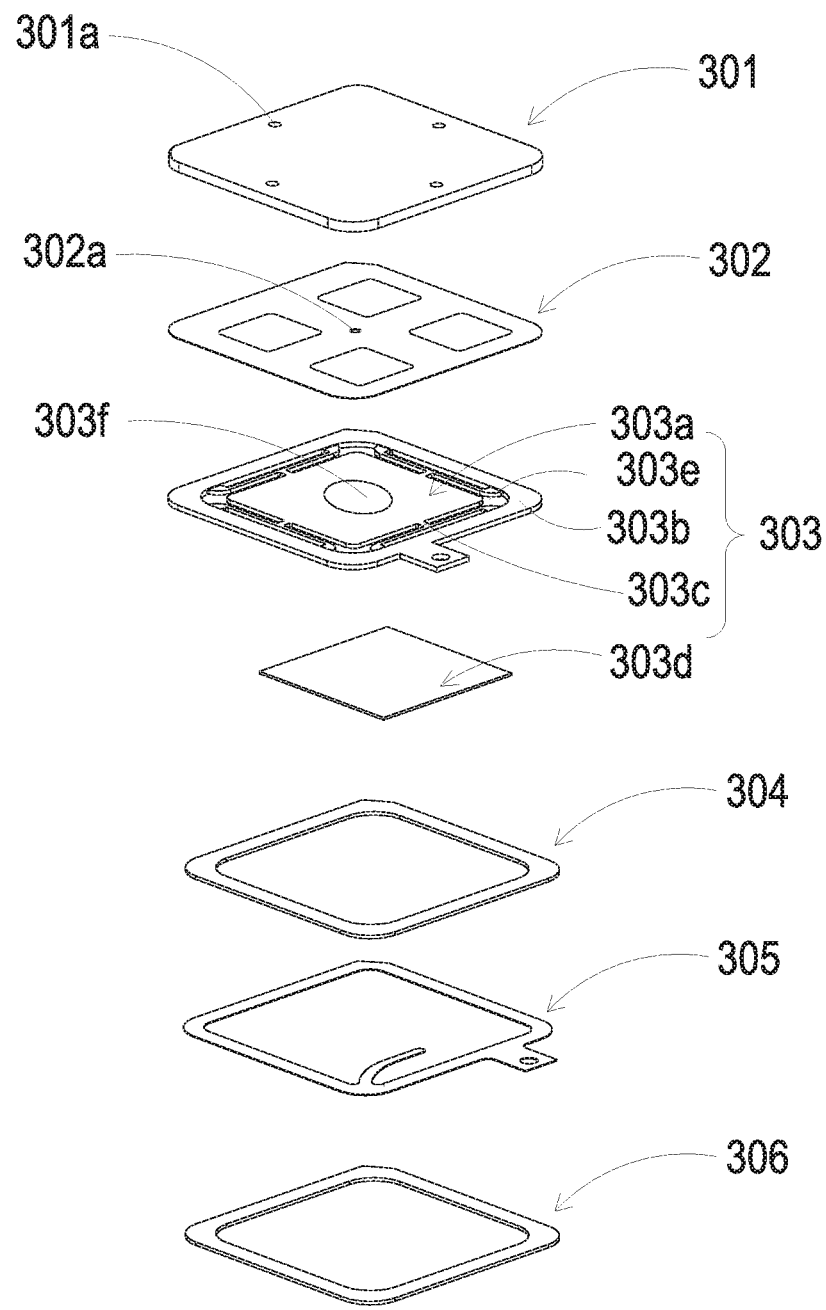
FIG. 3A illustrates a front exploded view of the gas-guiding unit of the gas detection and purification device in which the gas-guiding unit is an actuation pump of the exemplary embodiment.
Figure 3B:
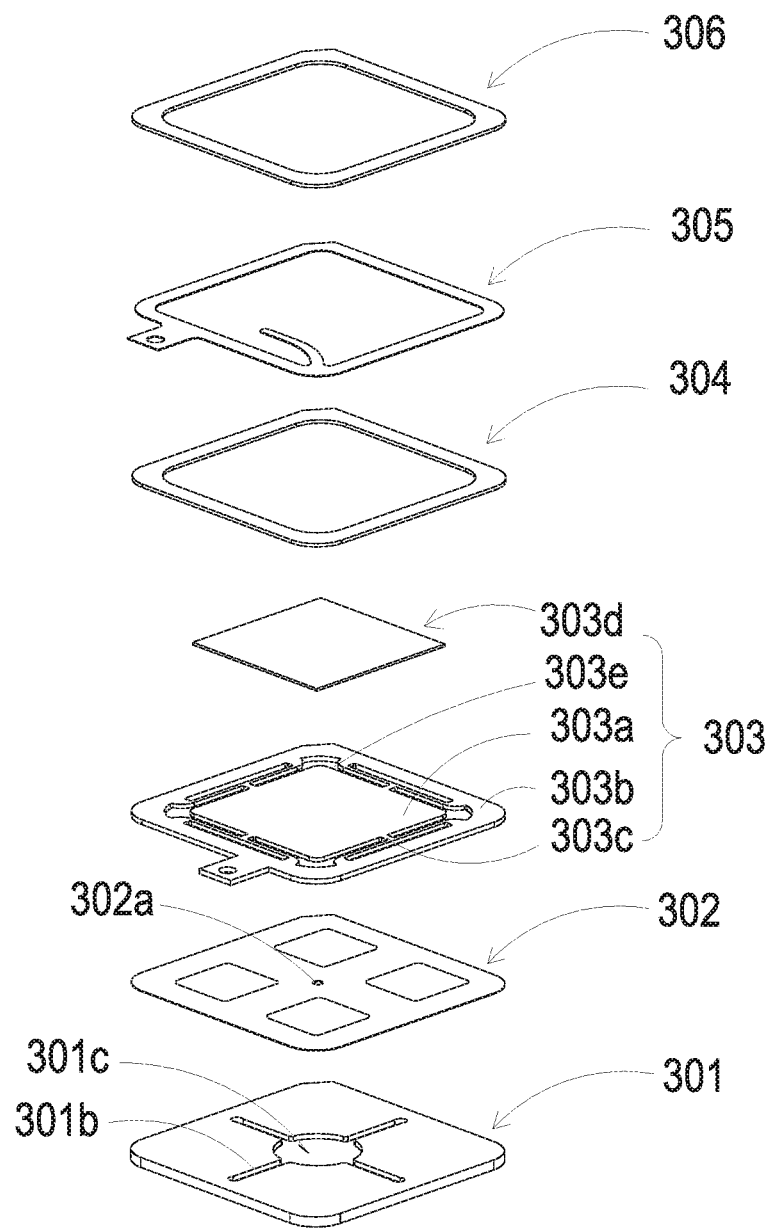
FIG. 3B illustrates a rear exploded view of the gas-guiding unit of the gas detection and purification device in which the gas-guiding unit is an actuation pump of the exemplary embodiment.
Figure 4A:
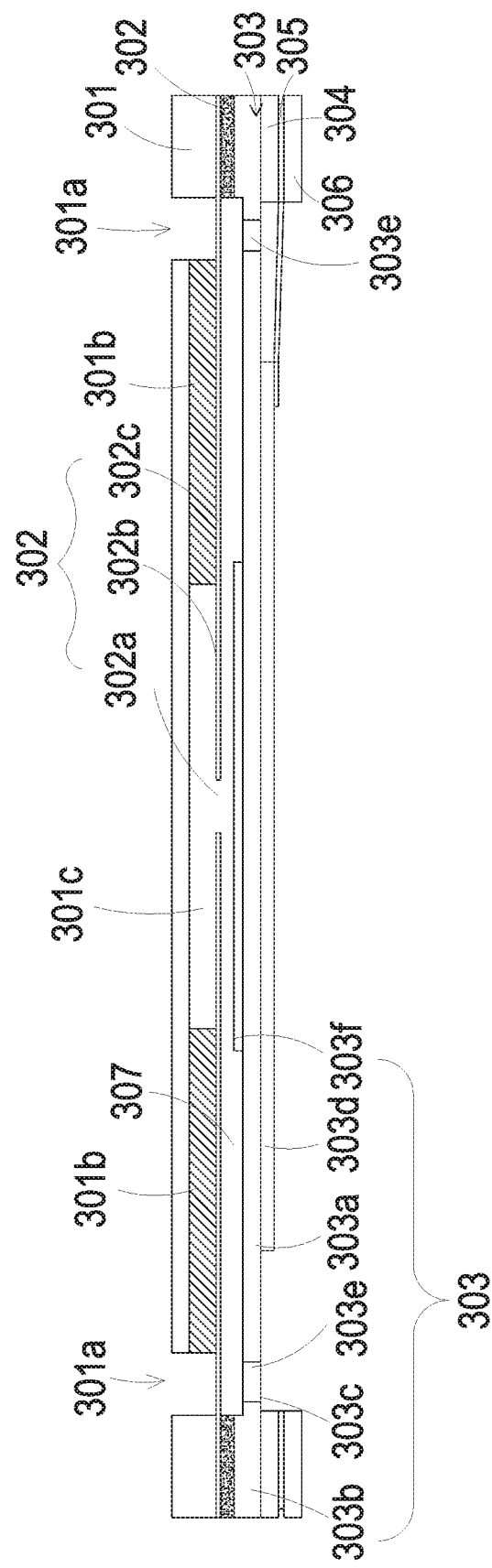
FIG. 4A illustrates a cross-sectional view of the actuation pump of the gas detection and purification device of the exemplary embodiment.

Please refer to FIG. 3A, FIG. 3B, and FIG. 4A. The resonance sheet 302 may be assembled on the inlet plate 301 by attaching. Furthermore, the resonance sheet 302 has a perforation 302a, a movable portion 302b, and a fixed portion 302c. The perforation 302a is located at a center portion of the resonance sheet 302 and corresponds to the convergence chamber 301c of the inlet plate 301. The movable portion 302b is disposed at a periphery of the perforation 302a and is disposed at a portion opposite to the convergence chamber 301a. The fixed portion 302c is disposed at an outer periphery of the resonance sheet 302 and attached to the inlet plate 301.

Please still refer to FIG. 3A, FIG. 3B, and FIG. 4A. The piezoelectric actuator 303 includes a suspension plate 303a, an outer frame 303b, at least one supporting element 303c, a piezoelectric element 303d, at least one gap 303e, and a protruding portion 303f In the embodiments of the present disclosure, the suspension plate 303a is in square shape. It is understood that, the reason why the suspension plate 303a adopts the square shape is that, comparing with a circle suspension plate having a diameter equal to the side length of the square suspension plate 303a, the square suspension plate 303a has an advantage of saving electricity. The power consumption of a capacitive load operated at a resonance frequency may increase as the resonance frequency increases, and since the resonance frequency of a square suspension plate 303a is much lower than that of a circular suspension plate, the power consumption of the square suspension plate 303a is relatively low as well. Consequently, the square design of the suspension plate 303a used in one or some embodiments of the present disclosure has the benefit of power saving. In the embodiments of the present disclosure, the outer frame 303b is disposed around the periphery of the suspension plate 303a. The at least one supporting element 303c is connected between the suspension plate 303a and the outer frame 303b to provide a flexible support for the suspension plate 303a. In the embodiments of the present disclosure, the piezoelectric element 303d has a side length, which is shorter than or equal to a suspension plate side length of the suspension plate 303a. The piezoelectric element 303d is attached to a surface of the suspension plate 303a so as to drive the suspension plate 303a to bend and vibrate when the piezoelectric element 303d is applied with a voltage. The at least one gap 303e is formed among the suspension plate 303a, the outer frame 303b, and the at least one connecting element 303c, and the at least one gap 303e is provided for the gas to flow therethrough. The protruding portion 303f is disposed on a surface of the suspension plate 303a opposite to the surface of the suspension plate 303a where the piezoelectric element 303d is attached. In this embodiment, the protruding portion 303f may be a convex structure protruding out from and integrally formed with the surface of the suspension plate 303a opposite to the surface of the suspension plate 303a where the piezoelectric element 303d is attached by performing an etching process on the suspension plate 303a.

Please still refer to FIG. 3A, FIG. 3B, and FIG. 4A. The inlet plate 301, the resonance plate 302, the piezoelectric actuator 303, the first insulation plate 304, the conductive plate 305, and the second insulation plate 306 are sequentially stacked and assembled. A chamber space 307 needs to be formed between the suspension plate 303a and the resonance plate 302. The chamber space 307 can be formed by filling a material between the resonance plate 302 and the outer frame 303b of the piezoelectric actuator 303, such as conductive adhesive, but not limited thereto. By filling a material between the resonance plate 302 and the suspension plate 303a, a certain distance can be maintained between the resonance plate 302 and the suspension plate 303a to form the chamber space 307, by which the gas can be guided to flow more quickly. Further, since an appropriate distance is maintained between the suspension plate 303a and the resonance plate 302, the interference raised by the contact between the suspension plate 303a and the resonance plate 302 can be reduced, so that the generation of noise can be decreased as well. In other embodiments, the needed thickness of the conductive adhesive between the resonance plate 302 and the outer frame 303b of the piezoelectric actuator 303 can be decreased by increasing the height of the outer frame 303b of the piezoelectric actuator 303. Accordingly, during the forming process at the hot pressing temperature and the cooling temperature, the situation that the actual spacing of the chamber space 307 being affected by the thermal expansion and contraction of the conductive adhesive can be avoided, thereby decreasing the indirect effect of the hot pressing temperature and the cooling temperature of the conductive adhesive on the entire structure of the actuation pump 30. Moreover, the height of the chamber space 307 also affects the transmission efficiency of the actuation pump 30. Therefore, it is important that a fixed height of the chamber space 307 should be maintained for the purpose of achieving stable transmission efficiency with the actuation pump 30.

Figure 4B:
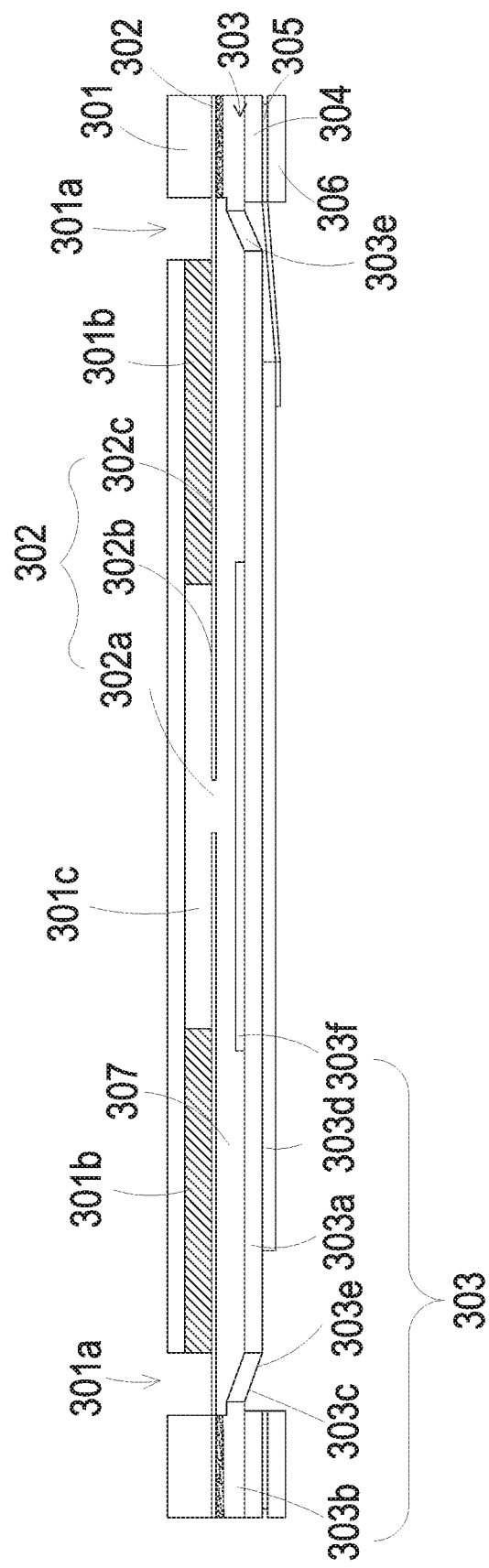
FIG. 4B illustrates a cross-sectional view of the actuation pump of the gas detection and purification device according to another exemplary embodiment of the present disclosure.

Therefore, as shown in FIG. 4B, in other embodiments of the piezoelectric actuator, the suspension plate 303a can be extended out by a certain distance by stamping. The extension distance can be adjusted by at least one supporting element 303c between the suspension plate 303a and the outer frame 303b so as to make the surface of the protruding portion 303f on the suspension plate 303a be not coplanar with the surface of the outer frame 303b. A few amount of filling material (such as the conductive adhesive) is applied on the assembly surface of the outer frame 303b, and the piezoelectric actuator 303 is assembled to the resonance plate 302 by attaching the piezoelectric actuator 303 onto the fixed portion 302c of the resonance plate 302 through hot pressing. By stamping the suspension plate 303a of the piezoelectric actuator 303 to form the chamber space 307, the chamber space 307 can be obtained by directly adjusting the extension distance of the suspension plate 303a of the piezoelectric actuator 303, which effectively simplifies the structural design of the chamber space 307, and also simplifies the manufacturing process and shortens the manufacturing time of the chamber space 307. Moreover, the first insulation plate 304, the conductive plate 305, and the second insulation plate 306 are all thin sheets with a frame like structure, and the first insulation plate 304, the conductive plate 305, and the second insulation plate 306 are sequentially stacked and assembled on the piezoelectric actuator 303 to form the main structure of the actuation pump 30.

Figure 4C:
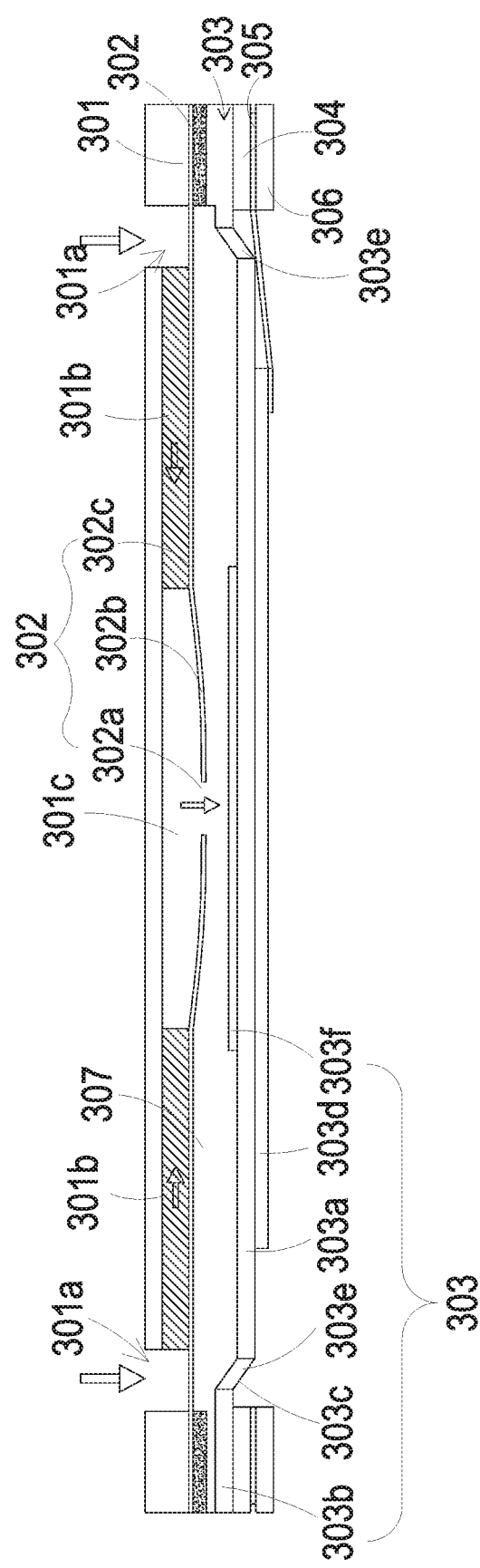
FIG. 4C to FIG. 4E illustrate schematic cross-sectional views showing the actuation pump of the gas detection and purification device shown in FIG. 4A at different operation steps.
Figure 4D:
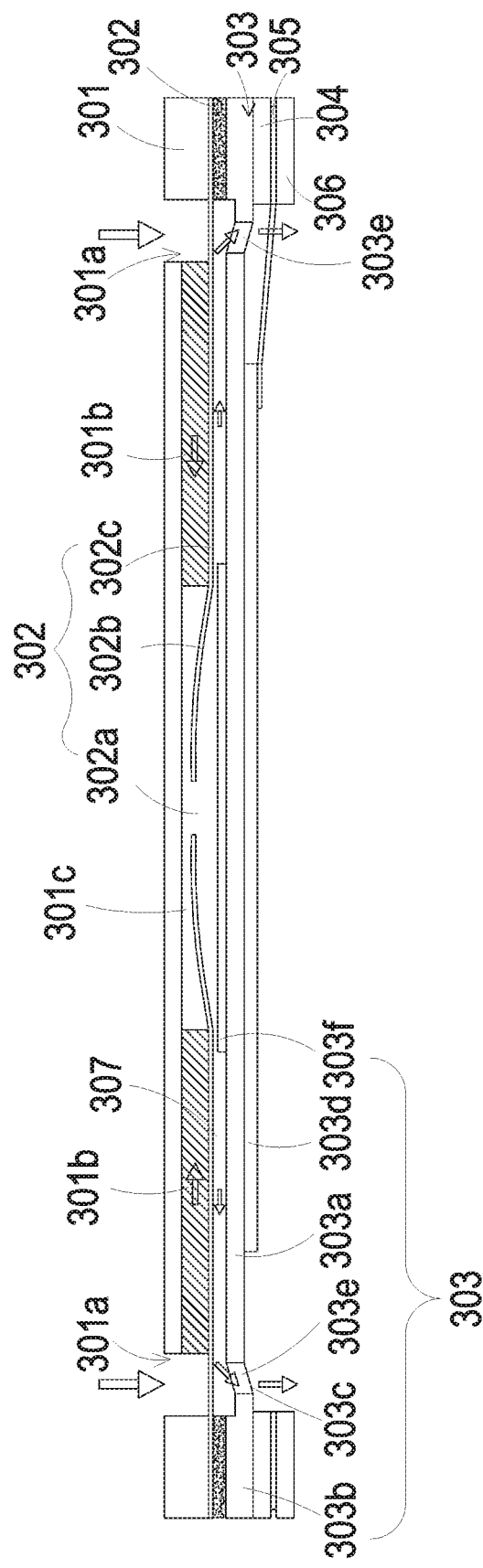
Figure 4E:
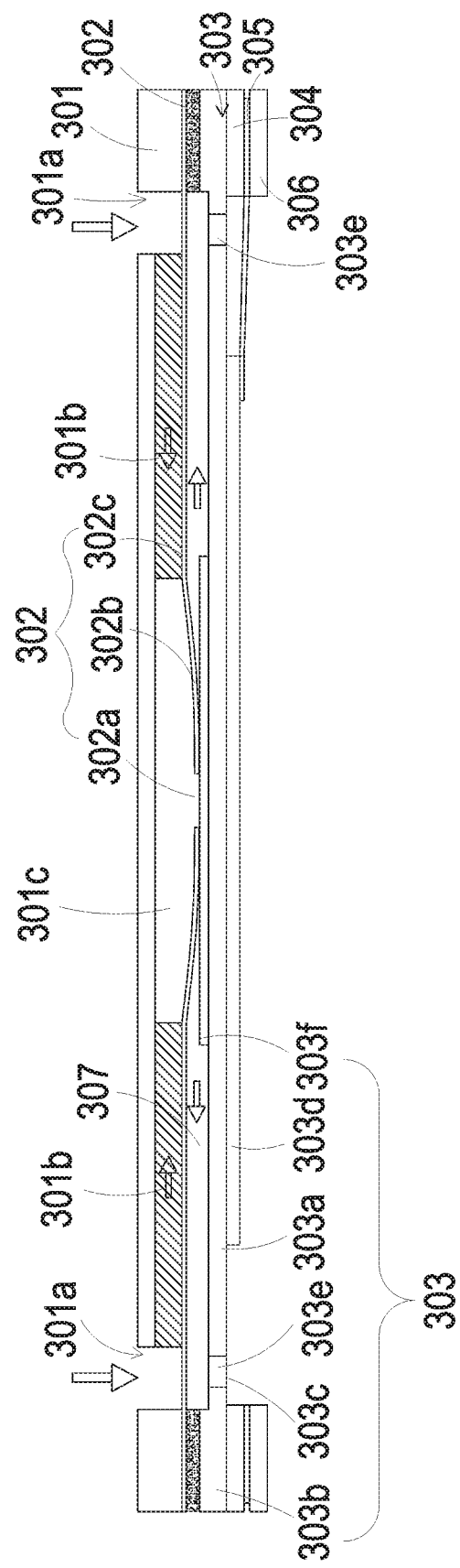

In order to understand the operation steps of the aforementioned actuation pump 30 in transmitting gas, please refer to FIG. 4C to FIG. 4E. Please refer to FIG. 4C first, the piezoelectric element 303d of the piezoelectric actuator 303 deforms after being applied with a driving voltage, and the piezoelectric element 303d drives the suspension plate 303a to move downwardly and to move away from the inlet plate 301. Thus, the volume of the chamber space 307 is increased and a negative pressure is generated inside the chamber space 307, thereby drawing the gas in the convergence chamber 301c into the chamber space 307. At the same time, owing to the resonance effect, the resonance sheet 302 moves downwardly is bent downwardly and away from the inlet plate 301 correspondingly, which also increases the volume of the convergence chamber 301c. Furthermore, since the gas inside the convergence chamber 301c is drawn into the chamber space 307, the convergence chamber 301c is in a negative pressure state as well. Therefore, the gas can be drawn into the convergence chamber 301c through the inlet hole 301a and the convergence channel 301b. Then, please refer to FIG. 4D. The piezoelectric element 303d drives the suspension plate 303a to move upwardly to move toward the inlet plate 301, thereby compressing the chamber space 307. Similarly, since the resonance sheet 302 resonates with the suspension plate 303a, the resonance sheet 302 also moves upwardly and moves toward the inlet plate 301, thereby pushing the gas in the chamber space 307 to be transmitted out of the actuation pump 30 through the at least one gap 303e so as to achieve gas transmission. Last, please refer to FIG. 4E. When the suspension plate 303a moves resiliently to its original position, the resonance sheet 302 still moves downwardly and moves away from the inlet plate 301 due to its inertia momentum. At the time, the resonance sheet 302 compresses the chamber space 307, so that the gas in the chamber space 307 is moved toward the gap 303e and the volume of the convergence chamber 301c is increased. Accordingly, the gas can be drawn into the convergence chamber 301c continuously through the inlet holes 301a and the convergence channels 301b and can be converged at the convergence chamber 301c. By continuously repeating the operation steps of the actuation pump 30 shown in FIG. 4C to FIG. 4E, the actuation pump 30 can make the gas continuously enter into the flow paths formed by the inlet plate 301 and the resonance sheet 302 from the inlet holes 301a, thereby generating a pressure gradient. The gas is then transmitted outward through the gap 303e. As a result, the gas can flow at a relatively high speed, thereby achieving the effect of gas transmission of the actuation pump 30.

Figure 13:
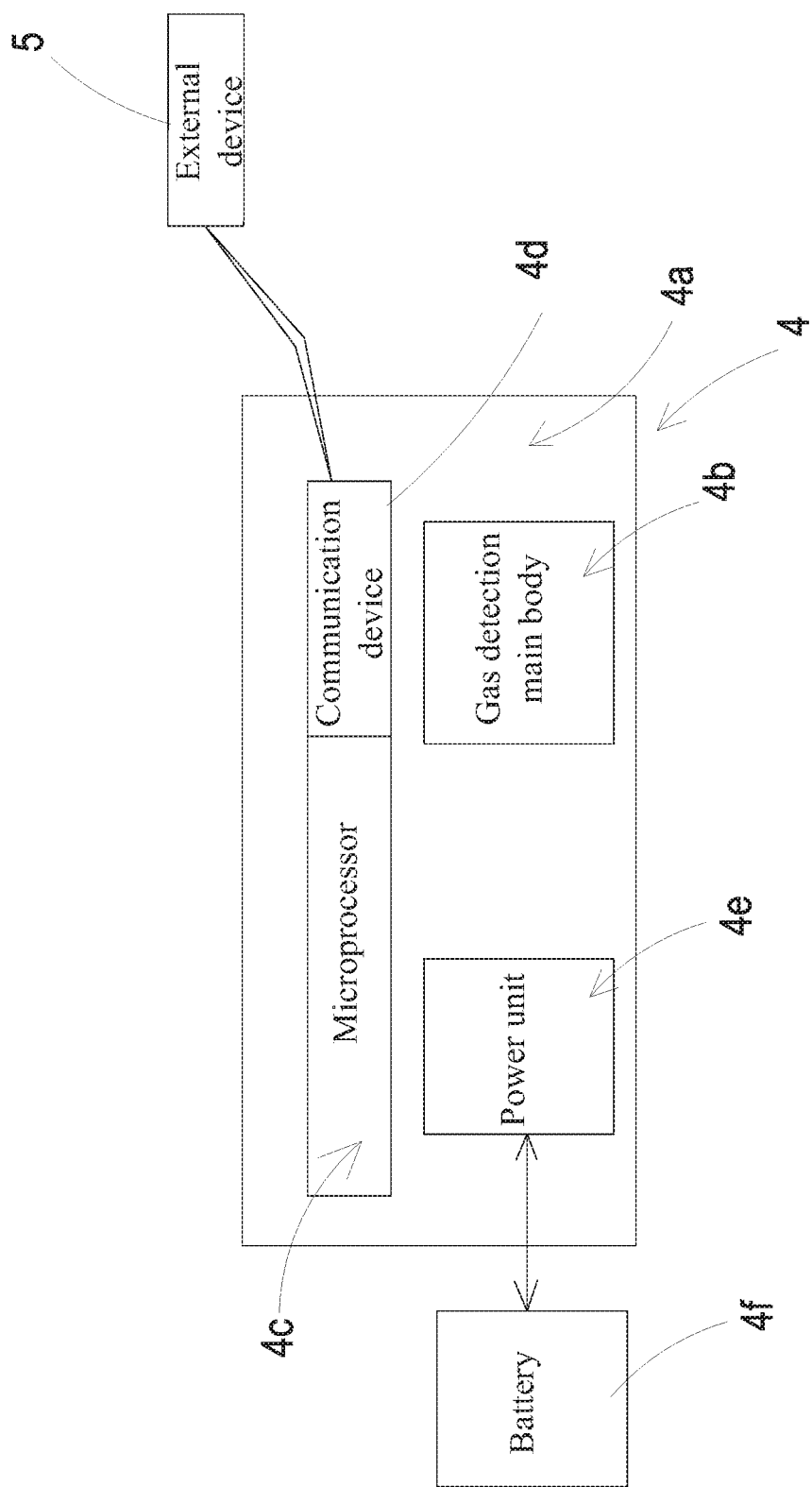
FIG. 13 illustrates a block diagram showing the relationships between the control circuit board and other components of the gas detection and purification device of the exemplary embodiment.

Furthermore, as shown in FIG. 5A to 5C, FIG. 6A and FIG. 6B, FIG. 7, FIG. 8A and FIG. 8B as well as FIG. 13, the gas detection module 4 includes a control circuit board 4a, a gas detection main body 4b, a microprocessor 4c, a communication device 4d, a power unit 4e, and a battery 4f. The gas detection main body 4b, the microprocessor 4c, the communication device 4d, and the power unit 4e are packaged with the control circuit board 4a, so that the gas detection main body 4b, the microprocessor 4c, the communication device 4d, and the power unit 4e are integrated with and electrically connected to the control circuit board 4a. The power unit 4e is used to provide power for operating the gas detection main body 4b, such that the gas detection main body 4b detects the guided gas inside the housing 1 so as to obtain gas detection data, and the power unit 4e is electrically connected to the battery 4f for obtaining the power. The microprocessor 4c receives the gas detection data to perform a computation processing to the gas detection data, and the microprocessor 4c controls the gas-guiding unit 3 to start or to stop operation for performing the operation of gas purification. The communication device 4d receives the gas detection data from the microprocessor 4c for transmitting the gas detection data to an external device 5, so that the external device 5 obtains information and a notification alert of the gas detection data. The external device 5 may be a mobile device, a cloud processing device, a computer device, or the like. The communication device 4d may perform the external communication transmission through wired communication transmission, for example, through USB interface connection to perform the communication transmission. Alternatively, the communication device 4d may perform the external communication transmission through wireless communication transmission, for example, through Wi-Fi communication transmission, Bluetooth communication transmission, wireless radio frequency identification (RFID) communication transmission, a near-field communication (NFC) transmission, or the like.

Figure 5A:
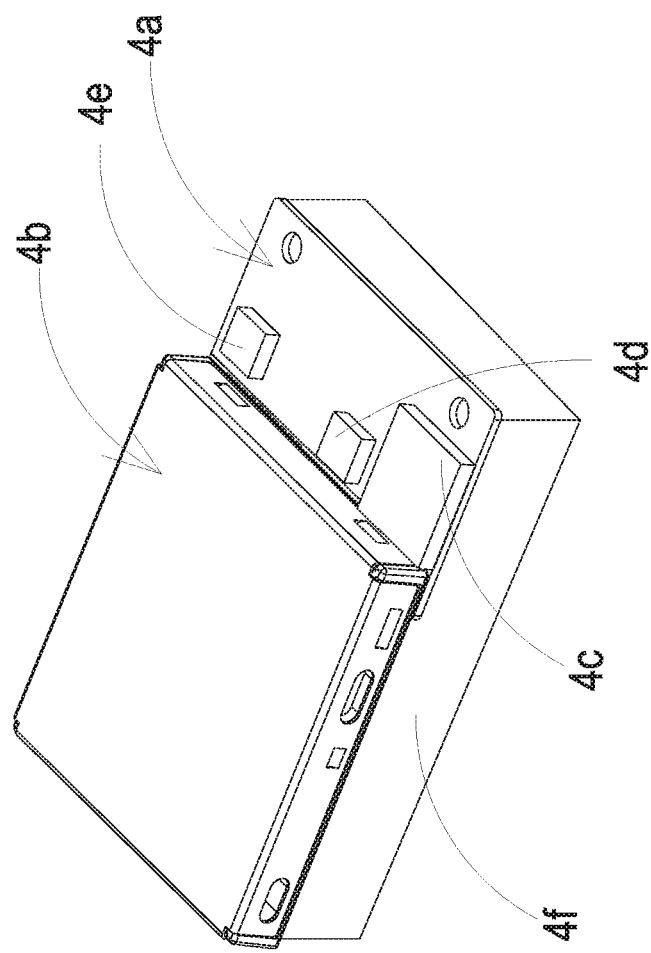
FIG. 5A illustrates a schematic perspective view of the gas detection module of the gas detection and purification device of the exemplary embodiment.
Figure 5B:
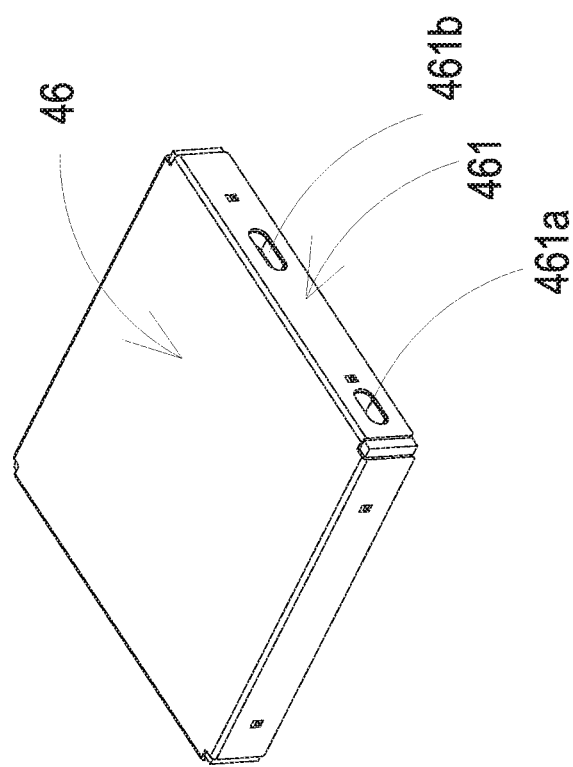
FIG. 5B illustrates a schematic perspective view of the gas detection main body of the gas detection module shown in FIG. 5A.
Figure 5C:
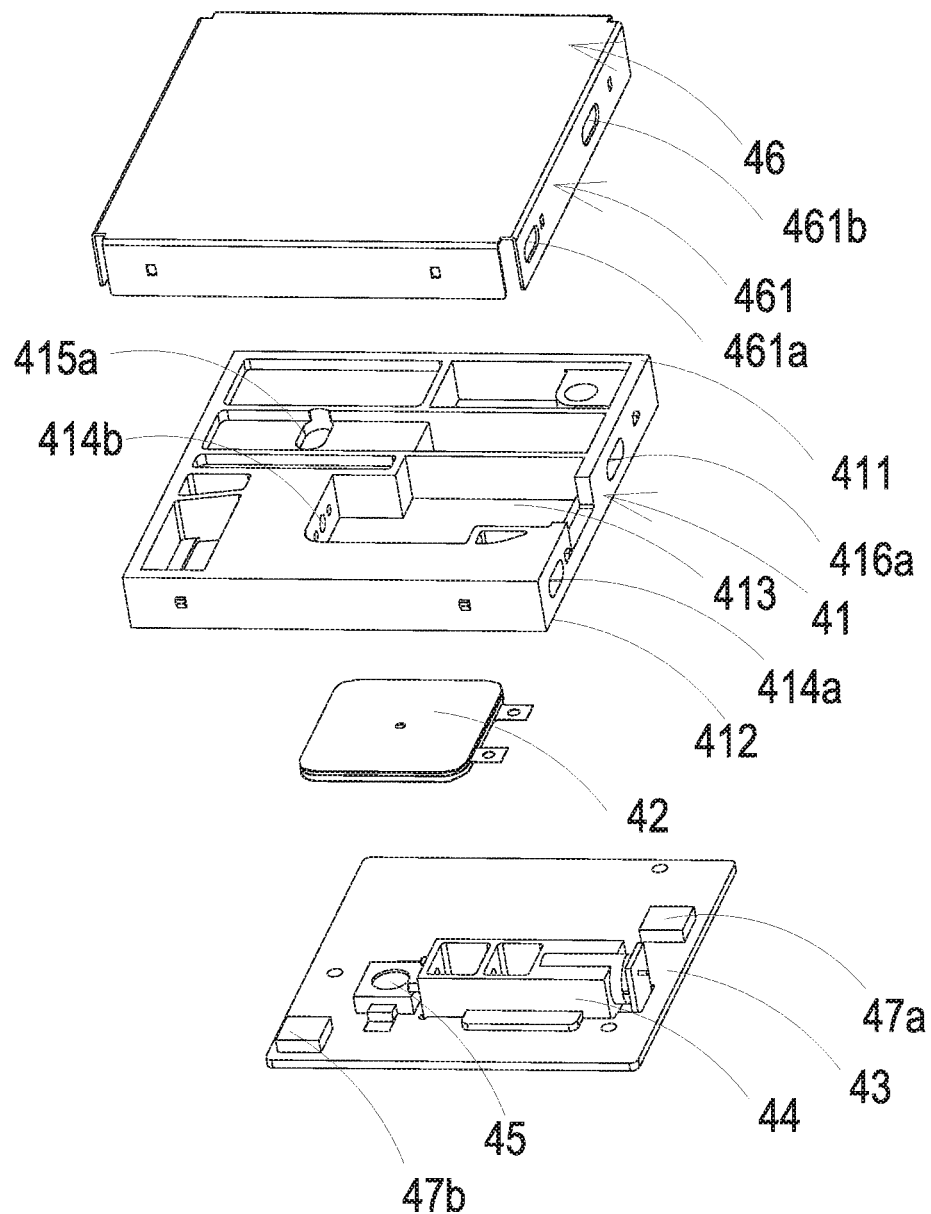
FIG. 5C illustrates an exploded view of the gas detection main body of the gas detection module shown in FIG. 5A.
Figure 6A:
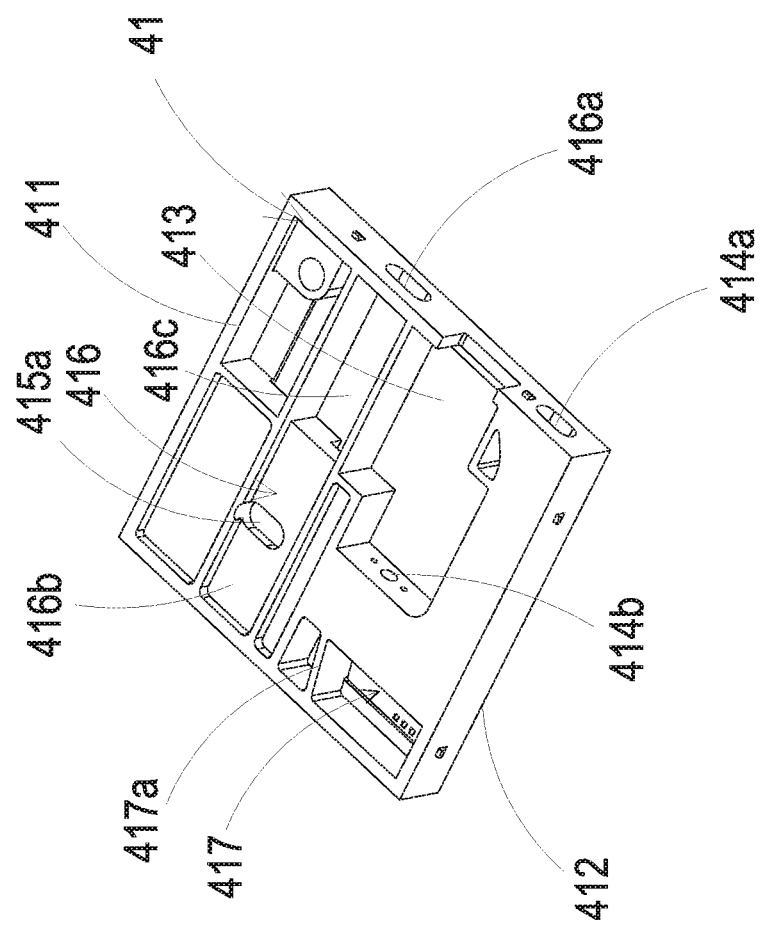
FIG. 6A illustrates a schematic perspective view of the base of the gas detection main body of the gas detection and purification device of the exemplary embodiment.
Figure 6B:
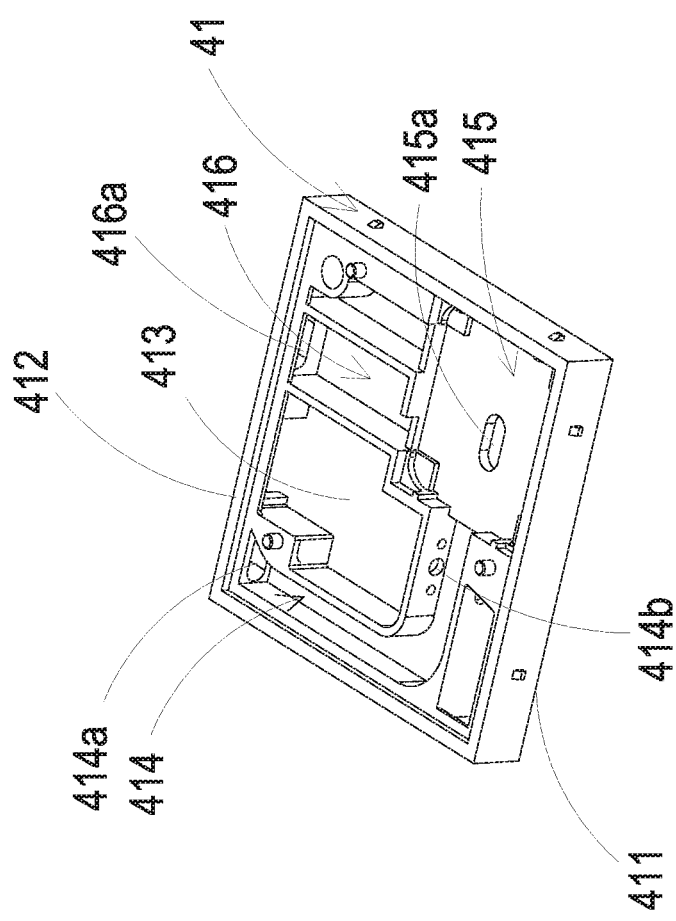
FIG. 6B illustrates a schematic perspective view of the base of the gas detection main body of the gas detection and purification device of the exemplary embodiment, from another perspective.
Figure 7:
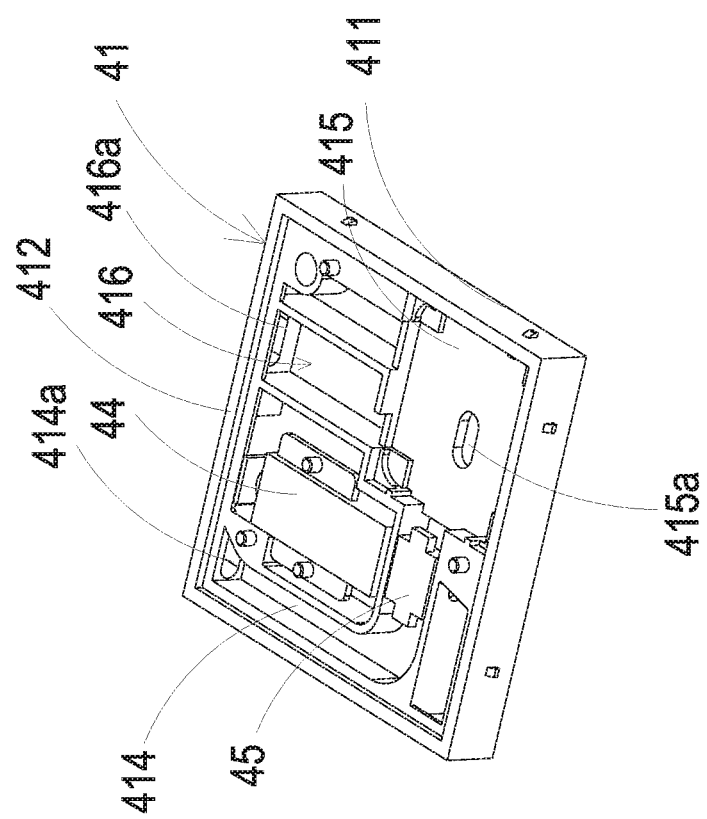
FIG. 7 illustrates a schematic perspective view showing that the laser component and the particulate sensor are received in the base of the gad detection main body of the exemplary embodiment.
Figure 11A:
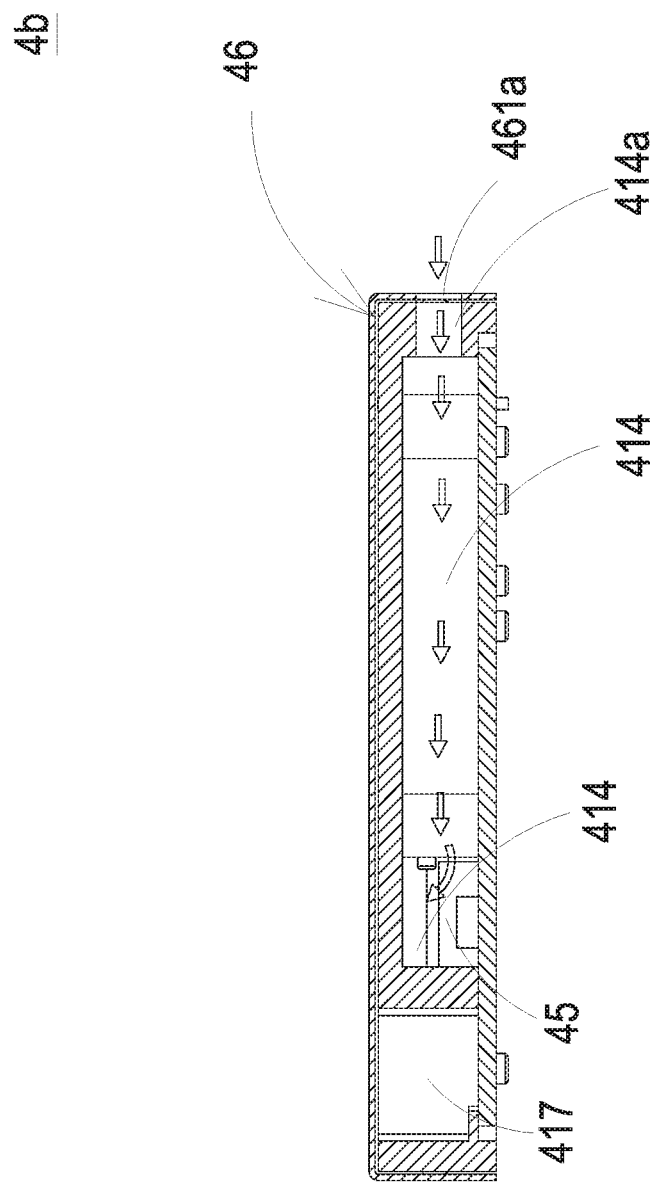
FIG. 11A to FIG. 11C illustrate schematic cross-sectional views showing the gas paths of the gas detection main body of the exemplary embodiment.
Figure 11B:
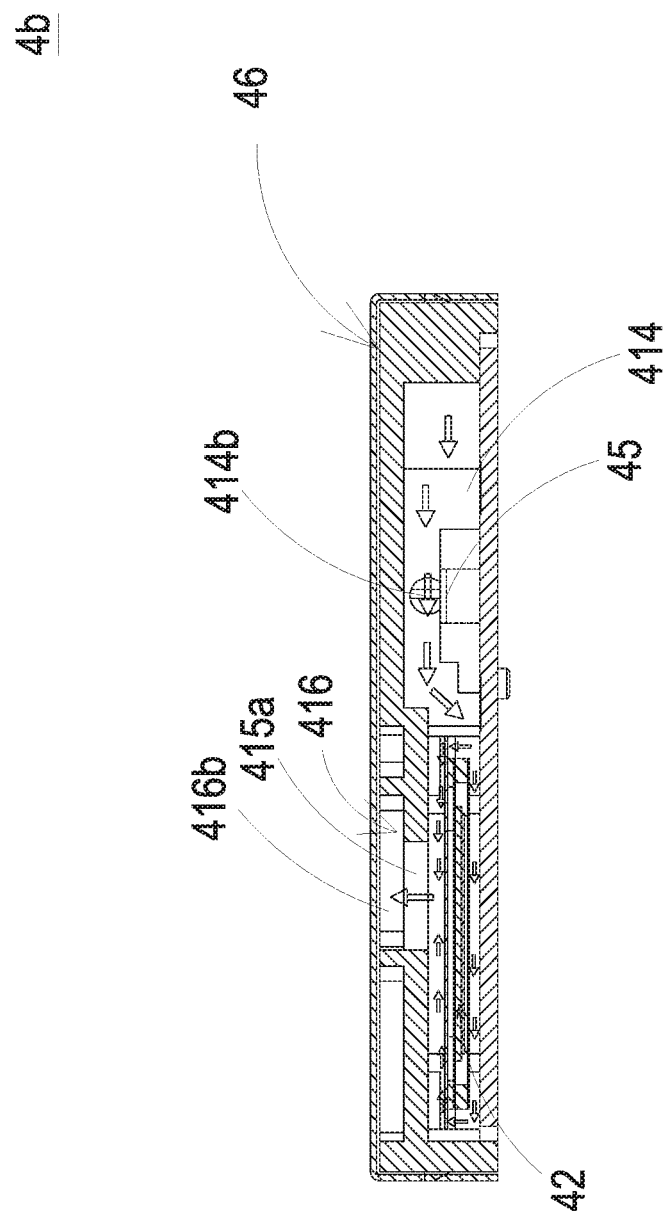
Figure 11C:
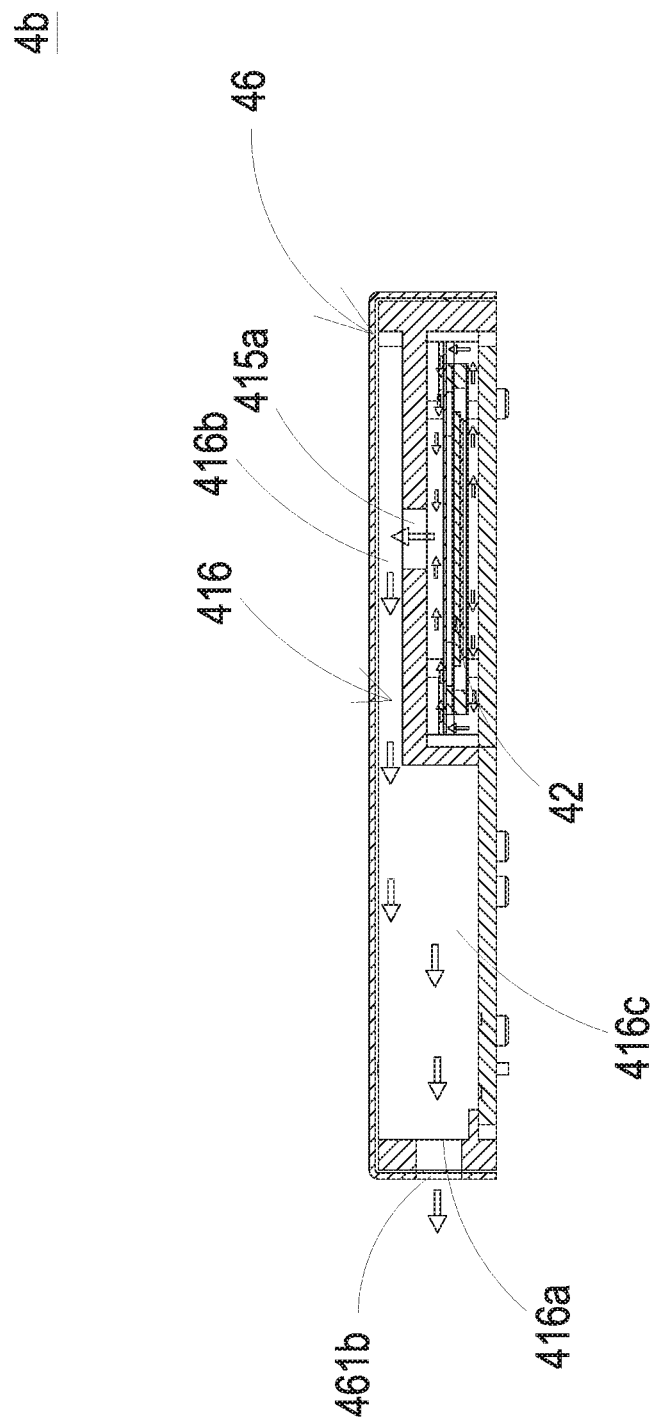

Further, as shown in FIG. 5A to 5C, FIG. 6A and FIG. 6B, FIG. 7, FIG. 8A to FIG. 8C, FIG. 9A and FIG. 9B as well as FIG. 11A to FIG. 11C, the gas detection main body 4b includes a base 41, a piezoelectric actuation element 42, a driving circuit board 43, a laser component 44, a particulate sensor 45, and an outer cap 46. The base 41 has a first surface 411, a second surface 412, a laser configuration region 413, a gas inlet groove 414, a gas-guiding component loading region 415, and a gas outlet groove 416. The first surface 411 and the second surface 412 are opposite surfaces. The laser configuration region 413 hollowed out from the first surface 411 to the second surface 412. Moreover, the outer cap 46 covers the base 41, and the outer cap 46 has a side plate 461. The side plate 461 has a gas inlet opening 461a and a gas outlet opening 461b. The gas inlet groove 414 is recessed from the second surface 412 and located adjacent to the laser configuration region 413. The gas inlet groove 414 has a gas inlet through hole 414a and two lateral walls. The gas inlet through hole 414a is in communication with outside of the base 41 and corresponds to the gas inlet opening 461a of the outer cap 46. A light permissive window 414b is opened on the lateral wall of the gas inlet groove 414 and is in communication with the laser configuration region 413. Therefore, the first surface 411 of the base 41 is covered by the outer cap 46, and the second surface 412 of the base 41 is covered by the driving circuit board 43, so that the gas inlet groove 414 and the driving circuit board 43 together define a gas inlet path (as shown in FIG. 7 and FIG. 11A).

Furthermore, as shown in FIG. 6A and FIG. 6B, the gas-guiding component loading region 415 is recessed from the second surface 412 and in communication with the gas inlet groove 414. A gas flowing hole 415a penetrates a bottom surface of the gas-guiding component loading region 415. The gas outlet groove 416 has a gas outlet through hole 416a, and the gas outlet through hole 416a corresponds to the gas outlet opening 461b of the outer cap 46. The gas outlet groove 416 includes a first region 416b and a second region 416c. The first region 416b is recessed from a portion of the first surface 411 corresponding to a vertical projection region of the gas-guiding component loading region 415. The second region 416c is at a portion extended from a portion not the vertical projection region of the gas-guiding component loading region 415, and the second region 416c is hollowed out from the first surface 411 to the second surface 412 in a region where the first surface 411 is not aligned with the gas-guiding component loading region 415. The first region 416b is connected to the second region 416c to form a stepped structure. Moreover, the first region 416b of the gas outlet groove 416 is in communication with the gas flowing hole 415a of the gas-guiding component loading region 415, and the second region 416c of the gas outlet groove 416 is in communication with the gas outlet through hole 416a. Therefore, when the first surface 411 of the base 41 is covered by the outer cap 46 and the second surface 412 of the base 41 is covered by the driving circuit board 43, the gas outlet groove 416, the outer cap 46, and the driving circuit board 43 together define a gas outlet path (as shown in FIG. 7 and FIG. 11).

Furthermore, as shown in FIG. 5C and FIG. 7, the laser component 44 and the particulate sensor 45 are disposed on the driving circuit board 43 and located in the base 41. Here, in order to clearly explain the positions of the laser component 44, the particulate sensor 45, and the base 41, the driving circuit board 43 is not illustrated in FIG. 7. Please refer to FIG. 5C, FIG. 6B, and FIG. 7. The laser component 44 is received in the laser configuration region 413 of the base 41. The particulate sensor 45 is received in the gas inlet groove 414 of the base 41 and aligned with the laser component 44. Moreover, the laser component 44 corresponds to the light permissive window 414b. The light permissive window 414b allows the light beam emitted by the laser component 44 to pass therethrough, so that the light beam further enters into the gas inlet groove 414. The path of the light beam emitted by the laser component 44 passes through the light permissive window 414b and is orthogonal to the gas inlet groove 414. The light beam emitted by the laser component 44 enters into the gas inlet groove 414 through the light permissive window 414b, and the particulate matters in the gas in the gas inlet groove 414 is illuminated by the light beam. When the light beam encounters the particulate matters, the light beam scatters to generate light spots. Hence, the particulate sensor 45 which is at a portion of the gas inlet groove 414 where the path of the light beam emitted by the laser component 44 is orthogonal to receives and calculates the light spots generated by the scattering, such that the particulate sensor 45 obtains the particle size and the concentration of the particulate matters in the gas and other related information. The particulate matters may include viruses and bacteria. The particulate sensor 45 may be a PM2.5 sensor.

Figure 8A:
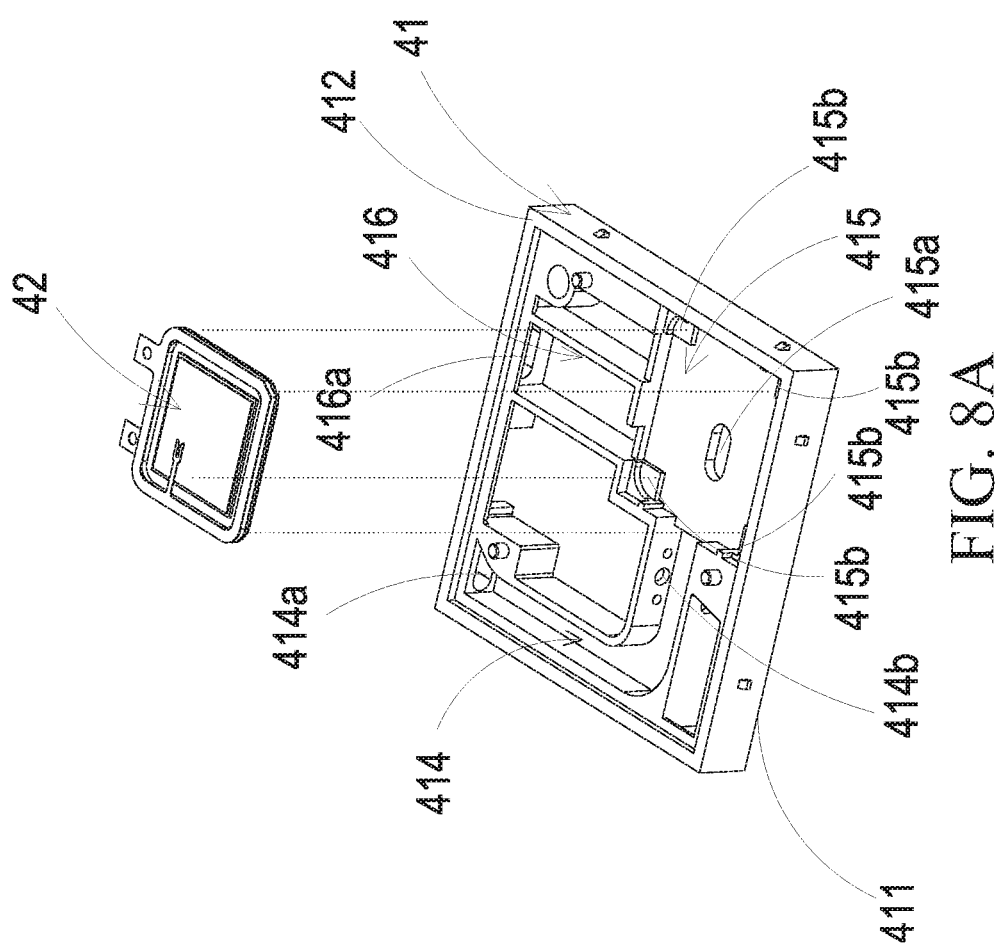
FIG. 8A illustrates an exploded view showing that the piezoelectric actuator is to be assembled with the base of the gas detection main body of the exemplary embodiment.
Figure 8B:
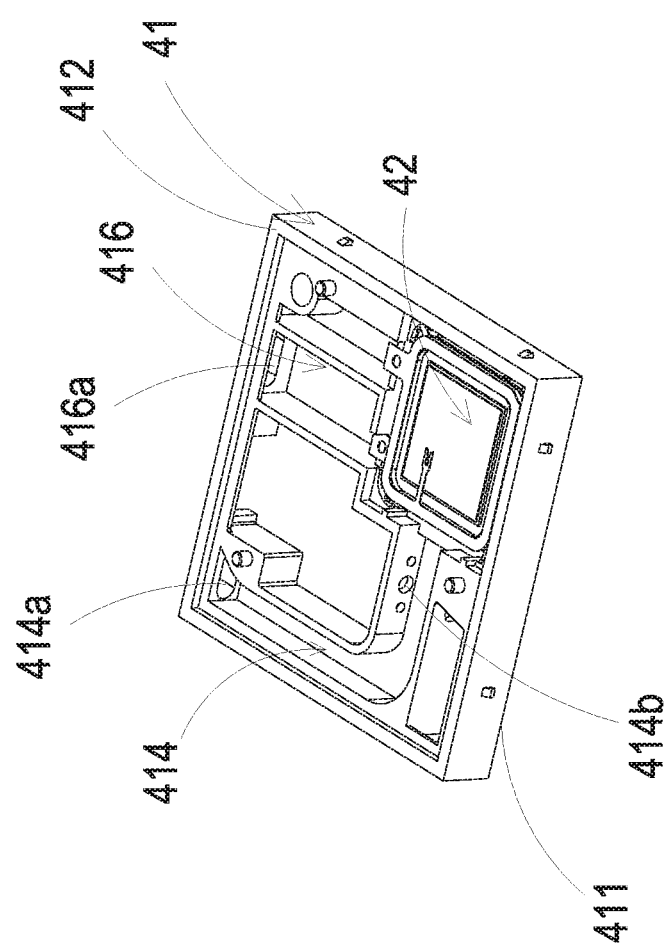
FIG. 8B illustrates a schematic perspective view showing that the piezoelectric actuator is assembled with the base of the gas detection main body of the exemplary embodiment.

Furthermore, as shown in FIG. 8A and FIG. 8B, the piezoelectric actuation element 42 is received in the gas-guiding component loading region 415 of the base 41. The gas-guiding component loading region 415 is a square, and each of four corners of the gas-guiding component loading region 415 has a positioning bump 415b. The piezoelectric actuation element 42 is disposed in the gas-guiding component loading region 415 through the four positioning bumps 415b. Furthermore, as shown in FIG. 6A, FIG. 6B, FIG. 11B, and FIG. 11C, the gas-guiding component loading region 415 is in communication with the gas inlet groove 414. When the piezoelectric actuation element 42 operates, the gas in the gas inlet groove 414 is drawn into the piezoelectric actuation element 42, and the gas passes through the gas flowing hole 415a of the gas-guiding component loading region 415 and enters into the gas outlet groove 416.

Furthermore, as shown in FIG. 5B and FIG. 5C, the driving circuit board 43 covers the second surface 412 of the base 41. The laser component 44 is disposed on the driving circuit board 43 and electrically connected to the driving circuit board 43. The particulate sensor 45 is also disposed on the driving circuit board 43 and electrically connected to the driving circuit board 43. As shown in FIG. 5B, when the outer cap 46 covers the base 41, the gas inlet opening 461a corresponds to the gas inlet through hole 414a of the base 41 (as shown in FIG. 11A), and the gas outlet opening 461b corresponds to the gas outlet through hole 416a of the base 41 (as shown in FIG. 11C).

Figure 9A:
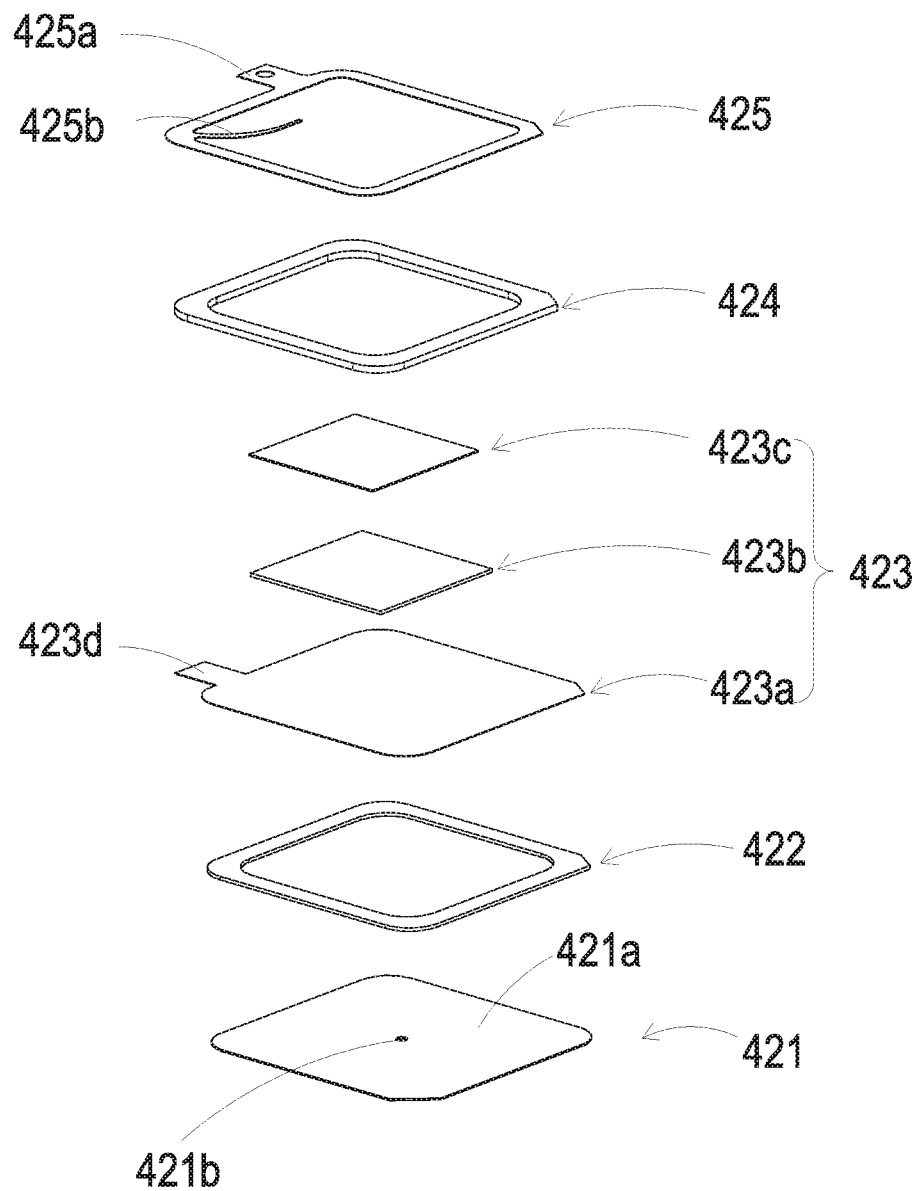
FIG. 9A illustrates an exploded view of the piezoelectric actuator of the gas detection main body of the exemplary embodiment.
Figure 9B:
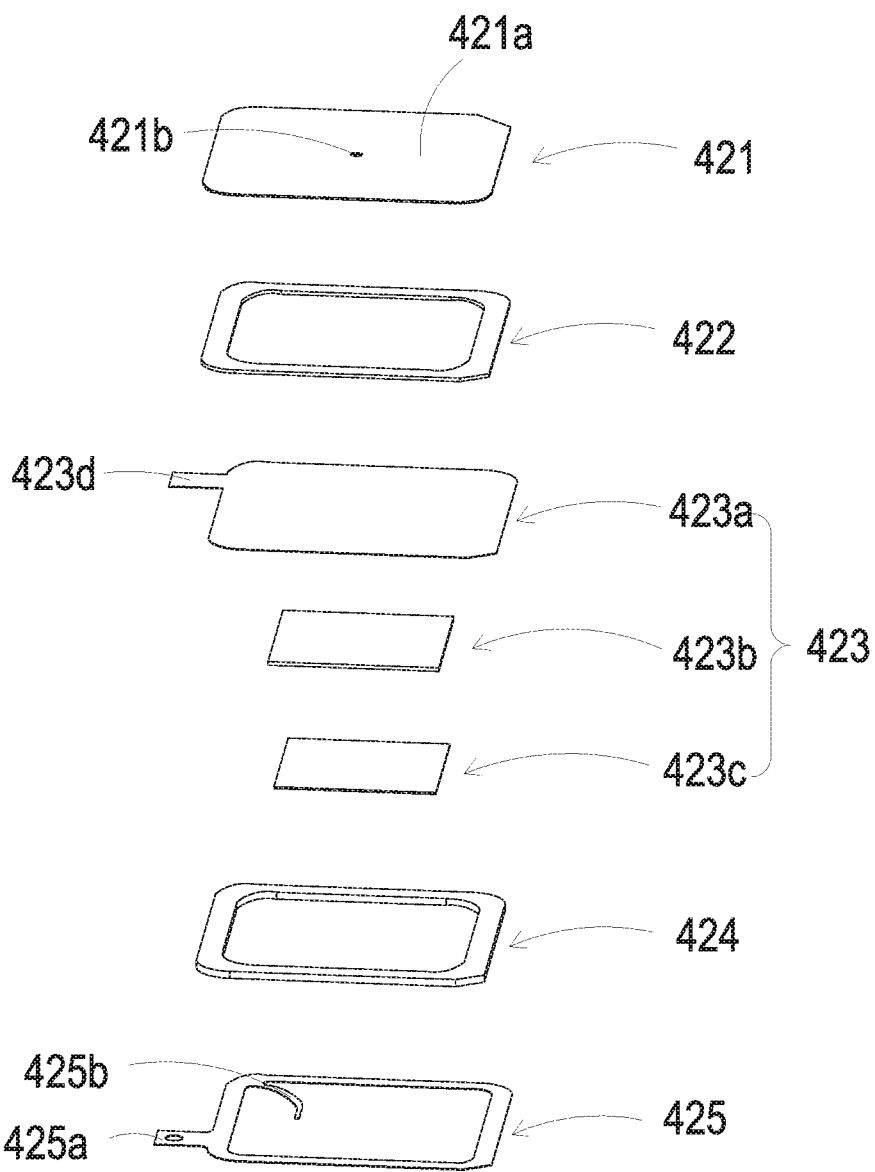
FIG. 9B illustrates an exploded view of the piezoelectric actuator of the gas detection main body of the exemplary embodiment, from another perspective.

Please refer to FIG. 9A and FIG. 9B. The piezoelectric actuation element 42 includes a nozzle plate 421, a chamber frame 422, an actuation body 423, an insulation frame 424, and a conductive frame 425. The nozzle plate 421 is made of a flexible material, and the nozzle plate 421 has a suspension sheet 421a and a hollow hole 421b. The suspension sheet 421a is a flexible sheet which can bend and vibrate. The shape and the size of the suspension sheet 421a approximately correspond to those of the inner edge of the gas-guiding component loading region 415, but embodiments are not limited thereto. The shape of the suspension sheet 421a may be one of square, circle, ellipse, triangle, and polygon. The hollow hole 421b penetrates the center portion of the suspension sheet 421a for allowing the gas flowing therethrough.

Figure 10A:
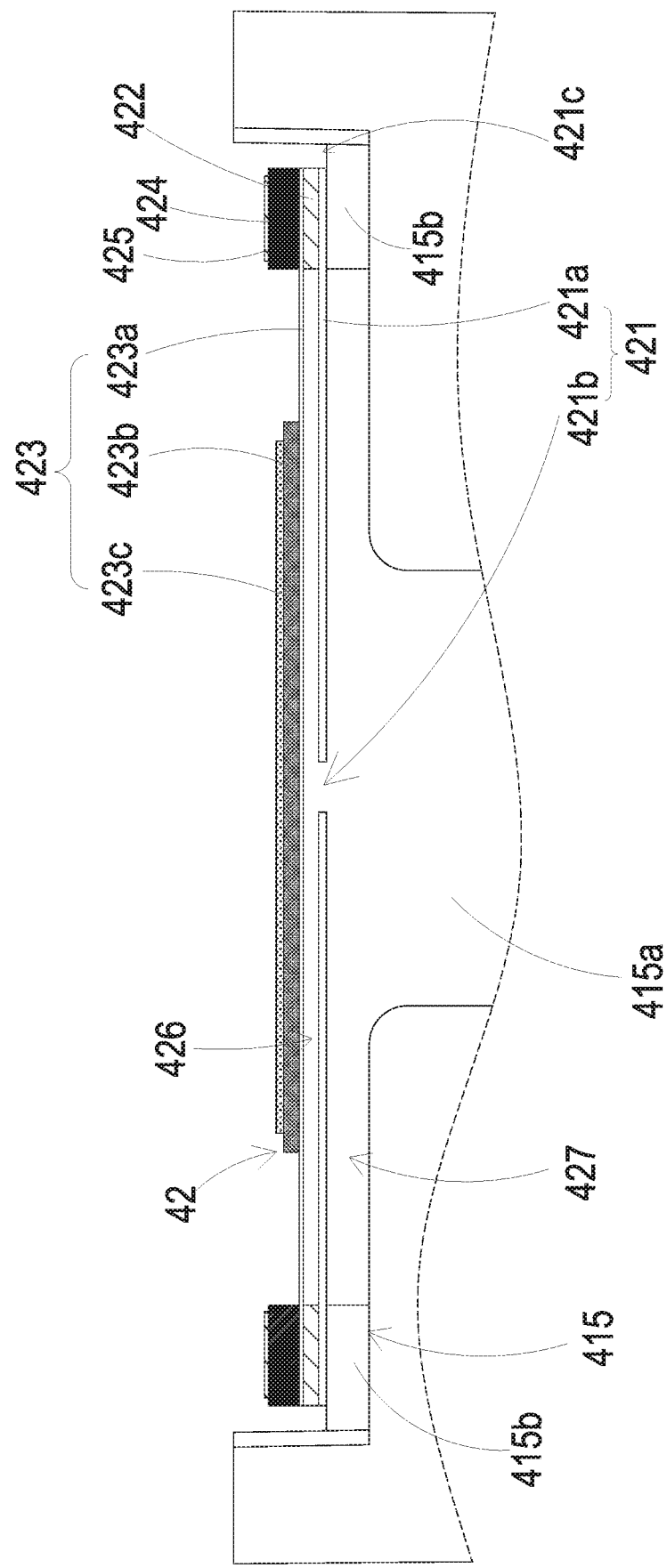
FIG. 10A illustrates a schematic cross-sectional view showing that the piezoelectric actuator of the gas detection main body is assembled with the gas-guiding component loading region of the exemplary embodiment.

Please refer to FIG. 9A, FIG. 9B, and FIG. 10A. The chamber frame 422 is stacked on the nozzle plate 421, and the shape of the chamber frame 422 corresponds to the shape of the nozzle plate 421. The actuation body 423 is stacked on the chamber frame 422. A resonance chamber 426 is between the chamber frame 422 and the suspension sheet 421a. The insulation frame 424 is stacked on the actuation body 423. The appearance of the insulation frame 424 is similar to that of the nozzle plate 421. The conductive frame 425 is stacked on the insulation frame 424. The appearance of the conductive frame 425 is similar to that of the insulation frame 424. The conductive frame 425 has a conductive frame pin 425a and a conductive electrode 425b. The conductive frame pin 425a extends outwardly from the outer edge of the conductive frame 425, and the conductive electrode 425b extends inwardly from the inner edge of the conductive frame 425. Moreover, the actuation body 423 further includes a piezoelectric carrier plate 423a, an adjusting resonance plate 423b, and a piezoelectric plate 423c. The piezoelectric carrier plate 423a is stacked on the chamber frame 422. The adjusting resonance plate 423b is stacked on the piezoelectric carrier plate 423a. The piezoelectric plate 423c is stacked on the adjusting resonance plate 423b. The adjusting resonance plate 423b and the piezoelectric plate 423c are accommodated in the insulation frame 424. The conductive electrode 425b of the conductive frame 425 is electrically connected to the piezoelectric plate 423c. The piezoelectric carrier plate 423a and the adjusting resonance plate 423b are both made of the same conductive material or different conductive materials. The piezoelectric carrier plate 423a has a piezoelectric pin 423d. The piezoelectric pin 423d and the conductive frame pin 425a are used for electrical connection so as to receive a driving signal (a driving frequency and a driving voltage), but is not limited thereto. The piezoelectric pin 423d, the piezoelectric carrier plate 423a, the adjusting resonance plate 423b, the piezoelectric plate 423c, the conductive electrode 425b, the conductive frame 425, and the conductive frame pin 425a may together form a loop, and the insulation frame 424 is provided for electrically isolating the conductive frame 425 and the actuation body 423 for avoiding short circuit, whereby the driving signal can be transmitted to the piezoelectric plate 423c. When the piezoelectric plate 423c receives the driving signal (a driving frequency and a driving voltage), the piezoelectric plate 423c deforms owing to the piezoelectric effect, and thus the piezoelectric carrier plate 423a and the adjusting resonance plate 423b are driven to perform reciprocating vibration correspondingly.

As mentioned above, the adjusting resonance plate 423b is disposed between the piezoelectric plate 423c and the piezoelectric carrier plate 423a. As a result, the adjusting resonance plate 423b can be served as a buffering element between the piezoelectric plate 423c and the piezoelectric carrier plate 423a, whereby the vibration frequency of the piezoelectric carrier plate 423a can be adjusted. Generally, the thickness of the adjusting resonance plate 423b is greater than the thickness of the piezoelectric carrier plate 423a. The thickness of the adjusting resonance plate 423b may be changed so as to adjust the vibration frequency of the actuation body 423.

Please refer to FIG. 9A, FIG. 9B, and FIG. 10A. The nozzle plate 421, the chamber frame 422, the actuation body 423, the insulation frame 424, and the conductive frame 425 are sequentially stacked and assembled with each other and are disposed in the gas-guiding component loading region 415, so that the piezoelectric actuation element 42 is placed and positioned in the gas-guiding component loading region 415. The bottom of the piezoelectric actuation element 42 is positioned with the positioning bumps 415b, so that the piezoelectric actuation element has a spacing distance 421c between the suspension sheet 421a and the inner edge of the gas-guiding component loading region 415 for the gas to pass therethrough.

Please refer to FIG. 10A first. A gas flow chamber 427 is formed between the nozzle plate 421 and the bottom surface of the gas-guiding component loading region 415. The gas flow chamber 427 is in communication with, through the hollow hole 421b of the nozzle plate 421, the resonance chamber 426 formed among the actuation body 423, the chamber frame 422, and the suspension sheet 421a. By controlling the vibration frequency of the gas in the resonance chamber 426 to be the same as the vibration frequency of the suspension sheet 421a, the resonance chamber 426 and the suspension sheet 421a can generate the Helmholtz resonance effect so as to improve the transmission efficiency of the gas.

Figure 10B:
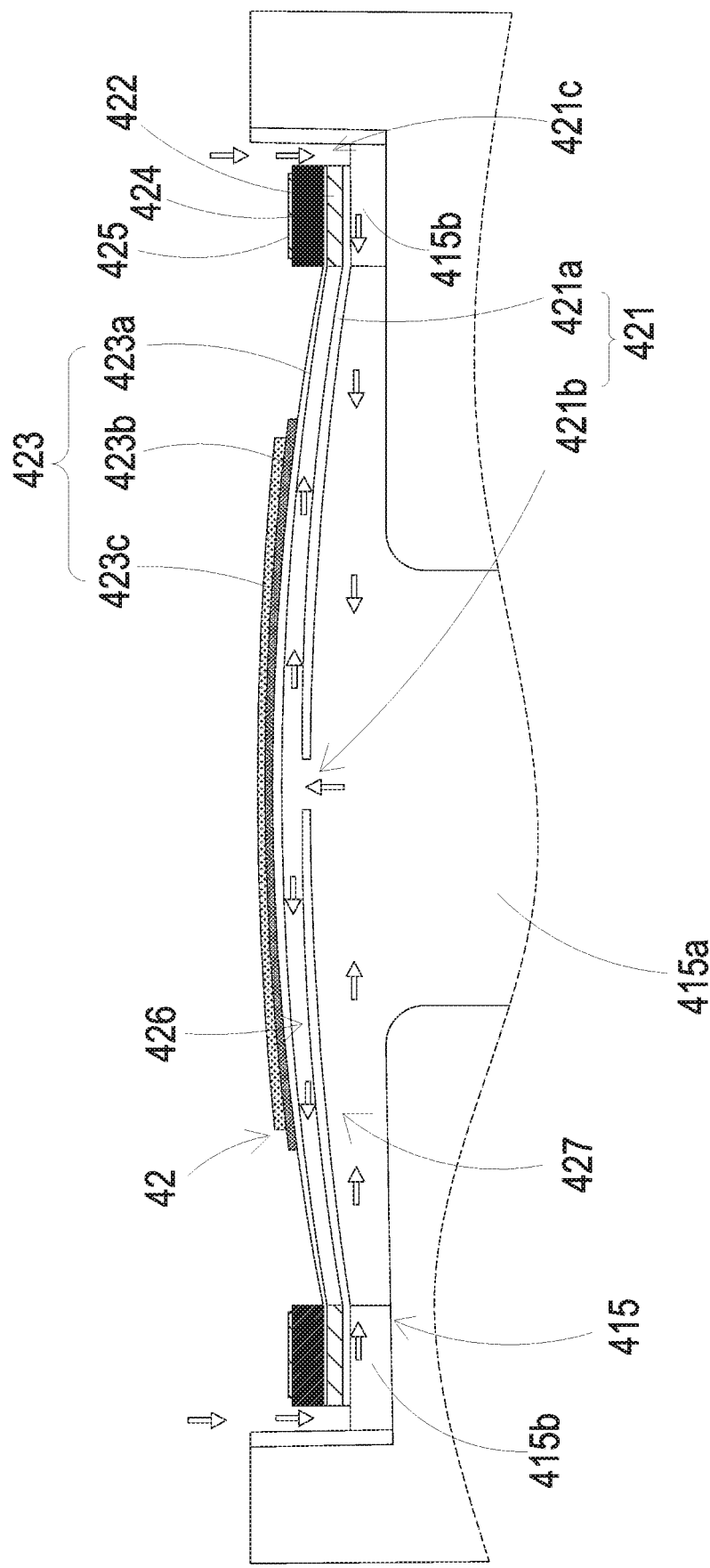
FIG. 10B and FIG. 10C illustrate schematic cross-sectional views showing the piezoelectric actuator shown in FIG. 10A at different operation steps.
Figure 10C:
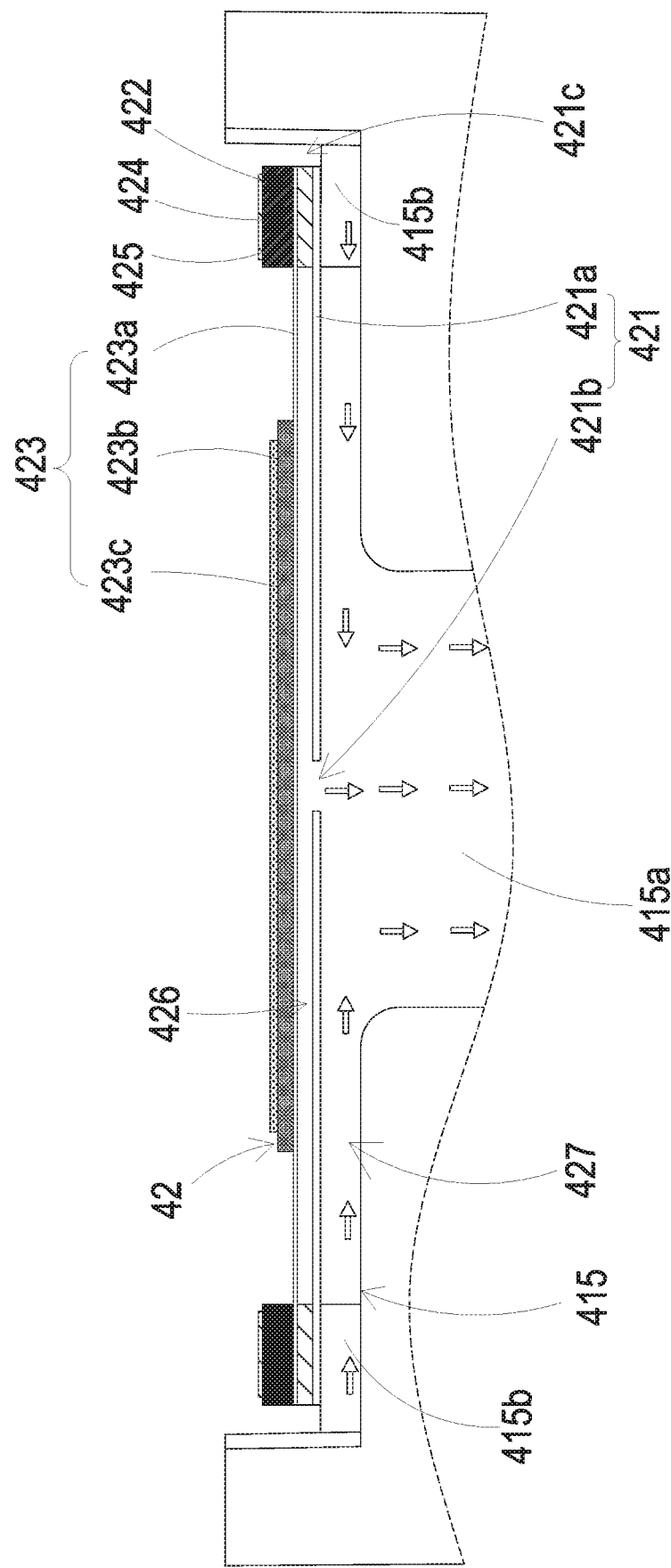

Please refer to FIG. 10B. When the piezoelectric plate 423c bends toward a direction away from the bottom surface of the gas-guiding component loading region 415, the suspension sheet 421a of the nozzle plate 421 is driven by the piezoelectric plate 423c to bend toward the direction away from the bottom surface of the gas-guiding component loading region 415 correspondingly. Hence, the volume of the gas flow chamber 427 expands quickly, so that the internal pressure of the gas flow chamber 427 decreases and becomes negative, thereby drawing the gas outside the piezoelectric actuation element 42 to flow into the piezoelectric actuation element 42 through the spacing distance 421c. The gas further enters into the resonance chamber 426 through the hollow hole 421b, thereby increasing the gas pressure of the resonance chamber 426 and thus generating a pressure gradient. Further, as shown in FIG. 10C, when the piezoelectric plate 423c drives the suspension sheet 421a of the nozzle plate 421 to move toward the bottom surface of the gas-guiding component loading region 415, the gas inside the resonance chamber 426 is pushed to flow out quickly through the hollow hole 421b so as to further push the gas inside the gas flow chamber 427, whereby the converged gas can be quickly and massively ejected and guided into the gas flowing hole 415a of the gas-guiding component loading region 415 in a state closing to an ideal gas state under the Bernoulli's law. Therefore, by repeating the steps as shown in FIG. 10B and FIG. 10C, the piezoelectric plate 423c can bend and vibrate reciprocatingly. Further, after the gas is discharged out of the resonance chamber 426, the internal pressure of the resonance chamber 426 is lower than the equilibrium pressure due to the inertia, thereby the pressure difference guiding the gas outside the resonance chamber 426 into the resonance chamber 426 again. Thus, by controlling the vibration frequency of the gas inside the resonance chamber 426 to be the same as the vibration frequency of the piezoelectric plate 423c in such way to generate the Helmholtz resonance effect, high-speed and large-volume gas transmission can be achieved.

Moreover, as shown in FIG. 11A, the gas enters into the gas detection main body 4 from the gas inlet opening 461a of the outer cap 46, passes through the gas inlet through hole 414a and enters into the gas inlet groove 414 of the base 41, and flows to the particulate sensor 45. As shown in FIG. 11B, the piezoelectric actuation element 42 continuously draws the gas in the gas inlet path so as to facilitate the gas outside the gas detection main body 4b to be guided therein and to pass over the particulate sensor 45. And, the light beam emitted by the laser component 44 passes through the light permissive window 414b and enters into the gas inlet groove 414. The gas in the gas inlet groove 414 passing over the particulate sensor 45 is illuminated by the light beam. When the light beam encounters the particulate matters in the gas, the light beam scatters to generate light spots. The particulate sensor 45 receives and calculates the light spots generated by the scattering, such that the particulate sensor 45 obtains the particle size and the concentration of the particulate matters in the gas and other related information. And, the gas passing over the particulate sensor 45 is continuously guided into the gas flowing hole 415a of the gas-guiding component loading region 415 by the driving of the piezoelectric actuation element 42 and enters into the first region 416b of the gas outlet groove 416. Last, as shown in FIG. 11C, after the gas enters into the first region 416b of the gas outlet groove 4166, since the piezoelectric actuation element 42 continuously delivers the gas into the first region 416b, the gas in the first region 416b is pushed toward the second region 416c, and the gas is eventually discharged out of the gas detection main body 4b through the gas outlet through hole 416a and the gas outlet opening 461b.

Figure 12:
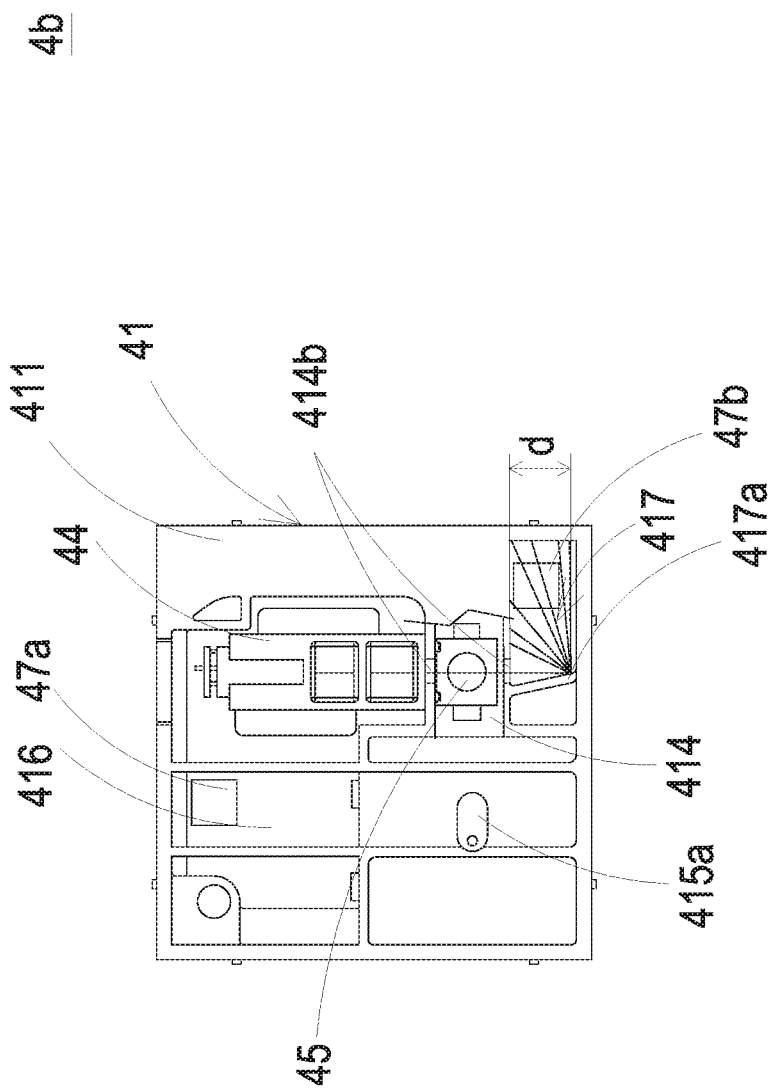
FIG. 12 illustrates a schematic cross-sectional view showing the laser beams emitted by the laser component of the gas detection main body of the exemplary embodiment.

Please refer to FIG. 12. The base 41 further includes a light trap region 417. The light trap region 417 is formed by hollowing out the base 41 from the first surface 411 toward the second surface 412, and the light trap region 417 corresponds to the laser configuration region 413. Moreover, the light trap region 417 passes through the light permissive window 414b, such that the light beam emitted by the laser component 44 can be projected into the light trap region 417. The light trap region 417 has a light trap structure 417a having an oblique cone surface, and the light trap structure 417a corresponds to the path of the light beam emitted by the laser component 44. Moreover, the light trap structure 417a allows the light beam emitted by the laser component 44 to be reflected to the light trap region 417 by the oblique cone surface of the light trap structure 417a, thereby preventing the light beam from being reflected to the particulate sensor 45. Moreover, a light trap distance d is maintained between the light permissive window 414b and the position where the light trap structure 417a receives the light beam, thereby preventing stray light beams from being directly reflected to the particulate sensor 45 after the light beam projecting on the light trap structure 417a is reflected, and thus causing the distortion of detection accuracy.

Please refer to FIG. 5C and FIG. 12. The gas detection module 4 according to one or some embodiments of the present disclosure is not only capable of detecting the particles in the gas, but also capable of detecting the features of the gas guided therein, for example, the gas may be formaldehyde, ammonia, carbon monoxide, carbon dioxide, oxygen, ozone, and so on. Therefore, in one or some embodiments of the present disclosure, the gas detection module 4 further includes a first volatile organic compound sensor 47a. The first volatile organic compound sensor 47a is disposed on the driving circuit board 43 and electrically connected to the driving circuit board 43, and the first volatile organic compound sensor 47a is received in the gas outlet groove 416 for detecting the gas guided out of the gas outlet path, so that the first volatile organic compound sensor 47a can be provided for detecting the concentration or the features of the volatile organic compound contained in the gas guided out of the gas outlet path. Alternatively, in one or some embodiments of the present disclosure, the gas detection module 4 further includes a second volatile organic compound sensor 47b. The second volatile organic compound sensor 47b is disposed on the driving circuit board 43 and electrically connected to the driving circuit board 43. The second volatile organic compound sensor 47b is received in the light trap region 417, and the second volatile organic compound sensor 47b is provided for detecting the concentration or the features of the volatile organic compound contained in the gas passing through the gas inlet path of the gas inlet groove 414 and guided into the light trap region 417 through the light permissive window 414b.

To sum up, one or some embodiments of the present disclosure provides a gas detection and purification device. The gas detection and purification device utilizes the gas detection module to detect ambient air quality in the car for the user anytime, and the gas detection and purification device provides a solution for air purification with the purification module. Accordingly, with the combinational application of the gas detection module and the purification module, the gas detection and purification device prevents the user in the in-car space or in the indoor space from breathing hazardous gases, and the user in the car or the indoor space can obtain information from the device so as to have proper prevention actions according to the notified information. Thus, the industrial value of the present application is very high, so the application is submitted in accordance with the law.

What is claimed is:

1. A gas detection and purification device, comprising:
a housing having at least one gas inlet and at least one gas outlet, wherein a gas channel is disposed between the at least one gas inlet and the at least one gas outlet;
a purification module disposed in the gas channel so as to filter a gas guided into the gas channel;
a gas-guiding unit disposed in the gas channel and disposed at one side of the purification module, wherein the gas-guiding unit guides the gas into the gas detection and purification device from the at least one gas inlet, guides the gas to pass through the purification module for performing filtering and purifying, and discharges the gas from the at least one gas outlet into an environment outside the gas detection and purification device; and
a gas detection module disposed in the gas channel, wherein the gas detection module comprises a control circuit board, a gas detection main body, a microprocessor, a communication device, a power unit, and a battery, and wherein the gas detection module is provided for detecting the gas guided into the housing to obtain gas detection data;
wherein the gas detection module performs a computation to process the gas detection data obtained by the gas detection module so as to control the gas-guiding unit to start or to stop operation, and
wherein when the gas-guiding unit is in operation, the gas-guiding unit guides the gas into the gas detection and purification device from the at least one gas inlet, guides the gas to pass through the purification module for performing filtering and purifying, and discharges the gas from the at least one gas outlet into the environment outside the gas detection and purification device to obtain a purified gas, whereby the gas detection and purification device provides a user with the purified gas, and wherein the gas detection main body comprises a base, and the base has:
a first surface;
a second surface opposite to the first surface;
a laser configuration region hollowed out from the first surface to the second surface; and
a gas inlet groove recessed from the second surface and located adjacent to the laser configuration region, wherein the gas inlet groove has a gas inlet through hole and two lateral walls, wherein a light permissive window is opened on a lateral wall of the gas inlet groove and is in communication with the laser configuration region.

2. The gas detection and purification device according to claim 1, wherein the purification module is a filtering unit.

3. The gas detection and purification device according to claim 2, wherein the filtering unit is one of an electrostatic filter, an activated carbon filter, and a high-efficiency particulate air (HEPA) filter.

4. The gas detection and purification device according to claim 2, wherein a purifying factor layer having chlorine dioxide is coated on the filtering unit for suppressing viruses and bacteria in the gas.

5. The gas detection and purification device according to claim 2, wherein an herbal protection coating layer consisting of *Rhus chinensis* Mill extracts from Japan and *Ginkgo biloba* extracts is coated on the filtering unit to form an herbal protection anti-allergy filter for performing an anti-allergy function and destroying cell surface proteins of influenza viruses passing through the herbal protection anti-allergy filter.

6. The gas detection and purification device according to claim 2, wherein a layer of silver ions is coated on the filtering unit for suppressing viruses and bacteria in the gas.

7. The gas detection and purification device according to claim 2, wherein the purification module consists of the filtering unit and a photocatalyst unit, and wherein the photocatalyst unit comprises a photocatalyst and an ultraviolet light, and the photocatalyst is excited under illumination of the ultraviolet light so as to degrade the gas guided into the gas detection and purification device, thereby filtering and purifying the gas.

8. The gas detection and purification device according to claim 2, wherein the purification module consists of the filtering unit and a photo plasma unit, wherein the photo plasma unit comprises a nanometer optical tube, and wherein the gas is illuminated by a light of the nanometer optical tube to degrade volatile organic gases in the gas, so that the gas guided into the gas detection and purification device is purified.

9. The gas detection and purification device according to claim 2, wherein the purification module consists of the filtering unit and a negative ion unit, and wherein the negative ion unit comprises at least one electrode wire, at least one dust-collecting plate, and a boost power supply, wherein the at least one electrode wire discharges electricity under a voltage so that particulates in the gas guided into the gas detection and purification device are adhered on the at least one dust-collecting plate, and the gas is filtered and purified.

10. The gas detection and purification device according to claim 2, wherein the purification module consists of the filtering unit and a plasma unit, wherein the plasma unit comprises an electric-field first protection mesh, an absorbing mesh, a high-voltage discharge electrode, an electric-field second protection mesh, and a boost power supply, and wherein the boost power supply provides the high-voltage discharge electrode with a voltage so as to generate a high-voltage plasma column, and plasma in the high-voltage plasma column degrades viruses or bacteria in the gas guided into the gas detection and purification device.

11. The gas detection and purification device according to claim 1, wherein the gas-guiding unit is a fan.

12. The gas detection and purification device according to claim 1, wherein the gas-guiding unit is an actuation pump.

13. The gas detection and purification device according to claim 12, wherein the actuation pump comprises:
- an inlet plate having at least one inlet hole, at least one convergence channel, and a convergence chamber, wherein the at least one inlet hole is used to guide the gas outside the actuation pump to flow therein, the at least one inlet hole correspondingly penetrates the at least one convergence channel, and the at least one convergence channel is converged at the convergence chamber, so that the gas guided from the at least one inlet hole is converged at the convergence chamber;
- a resonance sheet attached to the inlet plate, wherein the resonance sheet has a perforation, a movable portion, and a fixed portion, wherein the perforation is located at a center portion of the resonance sheet and corresponds to the convergence chamber of the inlet plate, the movable portion is disposed at a periphery of the perforation and is disposed at a portion opposite to the convergence chamber, and the fixed portion is disposed at an outer periphery of the resonance sheet and attached to the inlet plate; and
- a piezoelectric actuator attached on the resonance sheet and disposed correspondingly to the resonance sheet, wherein the piezoelectric actuator comprises:
- a suspension plate having a square shape, wherein the suspension plate is capable of bending and vibrating;
    - an outer frame disposed around a periphery of the suspension plate;
    - at least one supporting element connected between the suspension plate and the outer frame to provide a flexible support for the suspension plate; and
    - a piezoelectric element having a side length, wherein the side length of the piezoelectric element is smaller than or equal to a suspension plate side length of the suspension plate, and the piezoelectric element is attached to a surface of the suspension plate so as to apply a voltage to drive the suspension plate to bend and vibrate;
- wherein a chamber space is formed between the resonance sheet and the piezoelectric actuator, so that when the piezoelectric actuator is driven, the gas outside the actuation pump is guided into the actuation pump through the at least one inlet hole of the inlet plate, is converged at the convergence chamber via the at least one convergence channel, and flows through the perforation of the resonance sheet by a resonance effect between the piezoelectric actuator and the movable portion of the resonance sheet.

14. The gas detection and purification device according to claim 1, wherein the gas detection main body, the microprocessor, the communication device, and the power unit are packaged with the control circuit board, so that the gas detection main body, the microprocessor, the communication device, and the power unit are integrated with and electrically connected to the control circuit board, wherein the power unit is electrically connected to the battery for providing power for operating the gas detection main body, wherein the gas detection main body detects the guided gas inside the housing so as to obtain the gas detection data, wherein the microprocessor receives the gas detection data to perform a computation to process the gas detection data, and the microprocessor controls the gas-guiding unit to start or to stop operation, and wherein the communication device receives the gas detection data from the microprocessor for transmitting the gas detection data to an external device, so that the external device obtains information and a notification alert of the gas detection data; the external device being one selected from the group consisting of a mobile device, a cloud processing device, and a computer system.

15. The gas detection and purification device according to claim 1, wherein
- the base comprises:
    - a gas-guiding component loading region recessed from the second surface and in communication with the gas inlet groove, wherein a gas flowing hole penetrates a bottom surface of the gas-guiding component loading region, and each of four corners of the gas-guiding component loading region has a positioning bump; and
    - a gas outlet groove recessed from a portion of the first surface corresponding to the bottom surface of the gas-guiding component loading region, and hollowed out from the first surface to the second surface in a region where the first surface is not aligned with the gas-guiding component loading region, wherein the gas outlet groove is in communication with the gas flowing hole, and the gas outlet groove has a gas outlet through hole; and
- wherein the gas detection main body further comprises:
- a piezoelectric actuation element received in the gas-guiding component loading region;
- a driving circuit board attached to the second surface of the base;
- a laser component disposed on the driving circuit board and electrically connected to the driving circuit board, wherein the laser component is received in the laser configuration region, and wherein a path of a light beam emitted by the laser component passes through the light permissive window and is orthogonal to the gas inlet groove;
- a particulate sensor disposed on the driving circuit board and electrically connected to the driving circuit board, wherein the particulate sensor is received in a portion of the gas inlet groove where the path of the light beam emitted by the laser component is orthogonal thereto, so that the particulate sensor detects particulates passing through the gas inlet groove and illuminated by the light beam of the laser component; and
- an outer cap covering the first surface of the base, wherein the outer cap has a side plate, and wherein a portion of the side plate corresponding to the gas inlet through hole of the base has a gas inlet opening and another portion of the side plate corresponding to the gas outlet through hole of the base has a gas outlet opening, the gas inlet opening corresponds to the gas inlet through hole of the base, and the gas outlet opening corresponds to the gas outlet through hole of the base;
- wherein the outer cap is covered on the first surface of the base, and the driving circuit board is covered on the second surface of the base, so that the gas inlet groove defines a gas inlet path and the gas outlet groove defines a gas outlet path, thereby facilitating the piezoelectric actuation element to guide the gas out of the gas inlet through hole of the base to come into the gas inlet path defined by the gas inlet groove from the gas inlet opening, wherein the gas passes through the particulate sensor, so that the particulate sensor detects a particle concentration of the gas, and wherein the gas is transmitted by the piezoelectric actuation element, discharged into the gas outlet path defined by the gas outlet groove from the gas flowing hole, and is discharged out of the gas detection main body from the gas outlet through hole and the gas outlet opening of the base.

16. The gas detection and purification device according to claim 15, wherein the piezoelectric actuation element comprises:
   a nozzle plate comprising a suspension sheet and a hollow hole, wherein the suspension sheet is capable of bending and vibrating, and the hollow hole is formed at a center portion of the suspension sheet;
   a chamber frame stacked on the suspension sheet;
   an actuation body stacked on the chamber frame so as to bend and vibrate reciprocatingly when the actuation body is applied with a voltage, wherein the actuation body comprises:
      a piezoelectric carrier plate, stacked on the chamber frame;
      an adjusting resonance plate, stacked on the piezoelectric carrier plate; and
      a piezoelectric plate, stacked on the adjusting resonance plate so as to drive the piezoelectric carrier plate and the adjusting resonance plate to bend and vibrate reciprocatingly when the actuation body is applied with the voltage;
   an insulation frame stacked on the actuation body; and
   a conductive frame stacked on the insulation frame;
   wherein the nozzle plate is fixed on the positioning bumps in the gas-guiding component loading region, so that a spacing distance is defined between the nozzle plate and an inner side of the gas-guiding component loading region for the gas to flow therethrough; a gas flow chamber is formed between the nozzle plate and the bottom surface of the gas-guiding component loading region, and a resonance chamber is formed among the actuation body, the chamber frame, and the suspension sheet, and wherein the nozzle plate is capable of being driven to move correspondingly by driving the actuation body, so that the suspension sheet of the nozzle plate vibrates reciprocatingly, and thus the gas enters into the gas flow chamber through the spacing distance and then is discharged out of the gas flow chamber, thereby achieving transmission of the gas.

17. The gas detection and purification device according to claim 15, wherein the gas detection module further comprises a first volatile organic compound sensor and a second volatile organic compound sensor, wherein the first volatile organic compound sensor is disposed on the driving circuit board and electrically connected to the driving circuit board, and the first volatile organic compound sensor is received in the gas outlet groove for detecting the gas guided out of the gas outlet path, and wherein the second volatile organic compound sensor is disposed on the driving circuit board and electrically connected to the driving circuit board, the second volatile organic compound sensor is received in a light trap region of the base, and the second volatile organic compound sensor detects the gas passing through the gas inlet path of the gas inlet groove and guided into the light trap region through the light permissive window.

18. The gas detection and purification device according to claim 1, wherein a bottom portion of the housing is of a round cylinder structure, and wherein a diameter of the housing is in a range between 40 mm and 120 mm, and a height of the housing is in a range between 100 mm and 300 mm.

19. The gas detection and purification device according to claim 1, wherein a bottom portion of the housing is of a rectangular structure, and wherein a length of the housing is in a range between 40 mm and 120 mm, a width of the housing is in a range between 40 mm and 120 mm, and a height of the housing is in a range between 100 mm and 300 mm.

20. The gas detection and purification device according to claim 1, wherein the housing is portable and is disposed in an in-car receiving space, and wherein the in-car receiving space is one of a cup holder, a central console box, a trim platform near a front windshield, and a trim platform near a rear windshield.

21. The gas detection and purification device according to claim 1, wherein the housing is embedded in an in-car space, and wherein the in-car space is one of a speaker, an air conditioner outlet, a car door trim, an in-car trim, a seat, a headlining, a steering wheel, a receiving box, a rearview mirror, a sun visor, and a central console box.

* * * * *